(12) United States Patent
Perez-Perri et al.

(10) Patent No.: US 12,117,437 B2
(45) Date of Patent: Oct. 15, 2024

(54) ENHANCED RNA INTERACTOME CAPTURE (eRIC)

(71) Applicant: EUROPEAN MOLECULAR BIOLOGY LABORATORY, Heidelberg (DE)

(72) Inventors: Joel Ignazio Perez-Perri, Heidelberg (DE); Matthias W. Hentze, Heidelberg (DE); Birgit Rogell, Heidelberg (DE)

(73) Assignee: EUROPEAN MOLECULAR BIOLOGY LABORATORY (EMBL), Heidelberg (DE)

( * ) Notice: Subject to any disclaimer, the term of this patent is extended or adjusted under 35 U.S.C. 154(b) by 610 days.

(21) Appl. No.: 16/639,795

(22) PCT Filed: Aug. 17, 2018

(86) PCT No.: PCT/EP2018/072348
§ 371 (c)(1),
(2) Date: Feb. 18, 2020

(87) PCT Pub. No.: WO2019/034783
PCT Pub. Date: Feb. 21, 2019

(65) Prior Publication Data
US 2020/0209228 A1  Jul. 2, 2020

(30) Foreign Application Priority Data
Aug. 18, 2017 (EP) .................... 17186948

(51) Int. Cl.
*G01N 33/53* (2006.01)
*G01N 33/68* (2006.01)

(52) U.S. Cl.
CPC ......... *G01N 33/5308* (2013.01); *G01N 33/68* (2013.01)

(58) Field of Classification Search
CPC ............................ G01N 33/5308; G01N 33/68
See application file for complete search history.

(56) References Cited

PUBLICATIONS

Perez-Perri et al., "Discovery of RNA-binding proteins and characterization of their dynamic responses by enhanced RNA interactome capture," Nat. Commun., 2018, vol. 9, 4408, pp. 1-13.*
Castello et al., "System-wide identification of RNA-binding proteins by interactome capture," Nat. Protoc., 2013, vol. 8, No. 3, pp. 491-500.*
Jacobsen et al., "Direct isolation of poly(A)+ RNA from 4 M guanidine thiocyanate-lysed cell extracts using locked nucleic acid-oligo(T) capture," 2004, Nucleic Acids Res., 2004, vol. 32, No. 7, p. e64, pp. 1-10.*
Vester et al., "LNA (locked nucleic acid): high-affinity targeting of complementary RNA and DNA," Biochemistry, 2004, vol. 43, No. 42, pp. 13233-13241.*
Beckmann, Benedikt M. "RNA interactome capture in yeast," Methods vol. 118-119, pp. 82-92, Dec. 16, 2016.
Conrad, Thomas et al. "Serial interactome capture of the human cell nucleus," Nature Communications vol. 7, pp. 1-11, Apr. 4, 2016.
Rogell, Birgit et al. "Specific RNP capture with antisense LNA/DNA mixmers," vol. 23, No. 8, pp. 1290-1302, May 5, 2017.

* cited by examiner

*Primary Examiner* — Galina M. Yakovleva
(74) *Attorney, Agent, or Firm* — SALIWANCHIK, LLOYD & EISENSCHENK

(57) ABSTRACT

The present invention relates to an improved method of detecting RNA-binding proteins (RBPs) in cells, tissues or organisms, comprising the use of oligonucleotides comprising locked nucleic acid (LNA)-nucleotide analogues in the sequence thereof.

11 Claims, 25 Drawing Sheets
(21 of 25 Drawing Sheet(s) Filed in Color)
Specification includes a Sequence Listing.

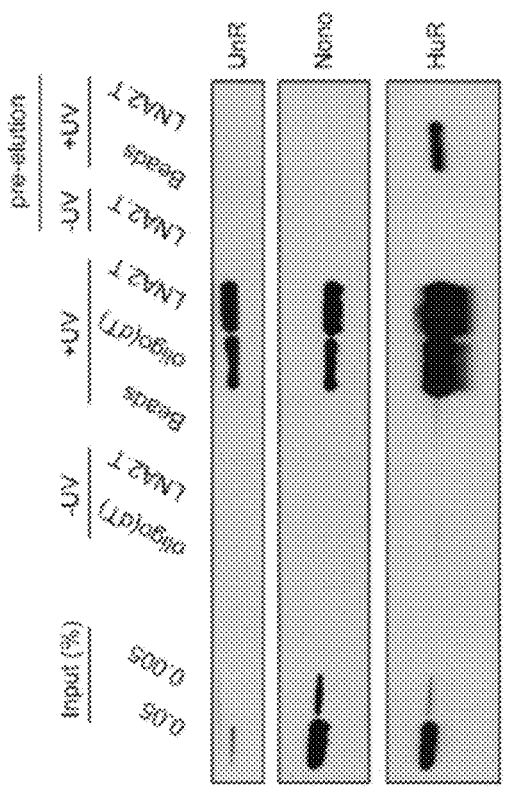
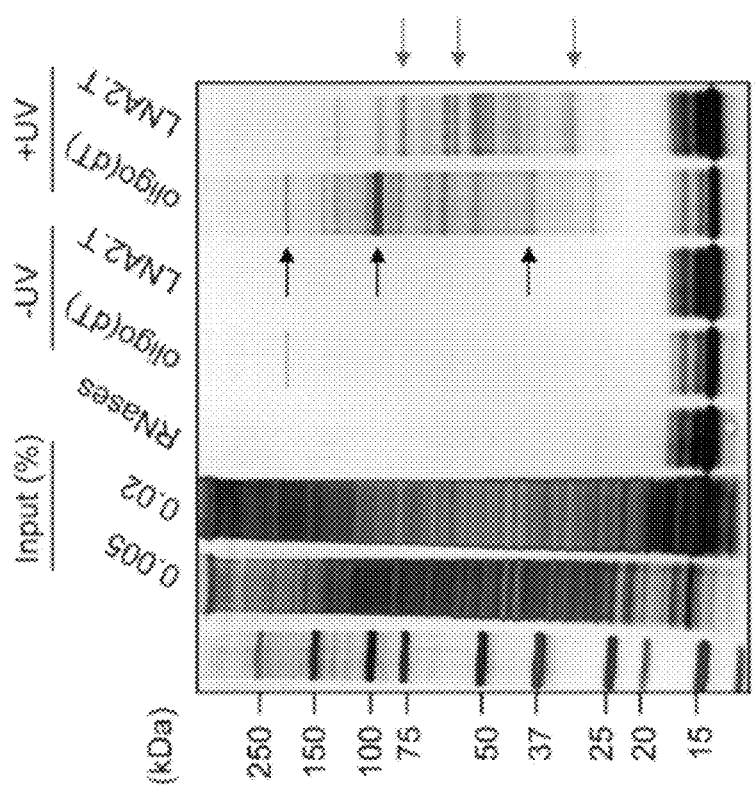
FIG. 7A
FIG. 7B

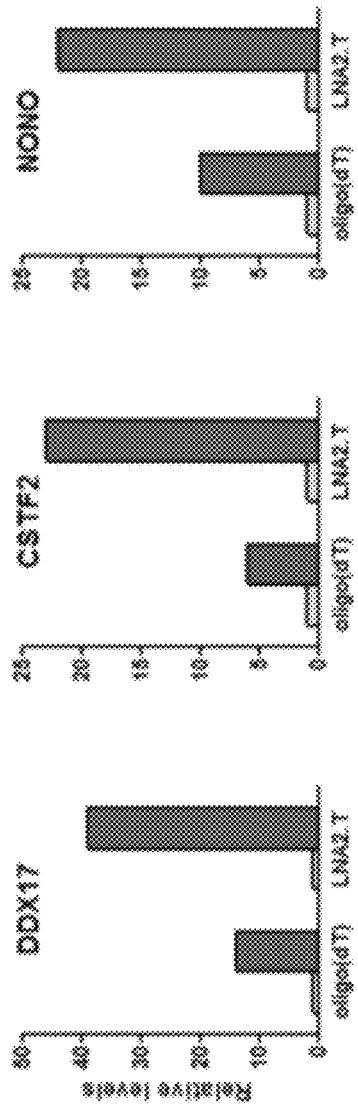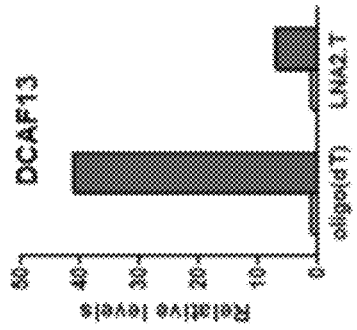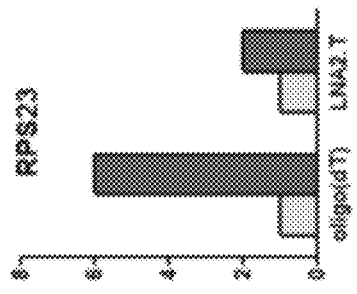
FIG. 8C

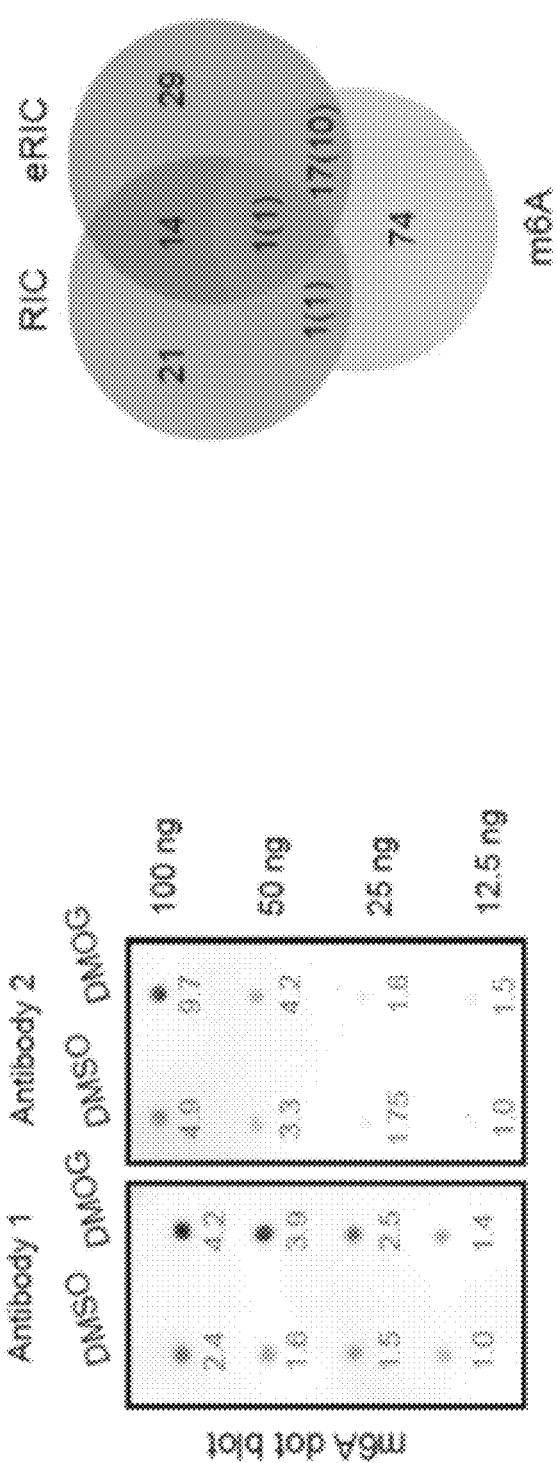
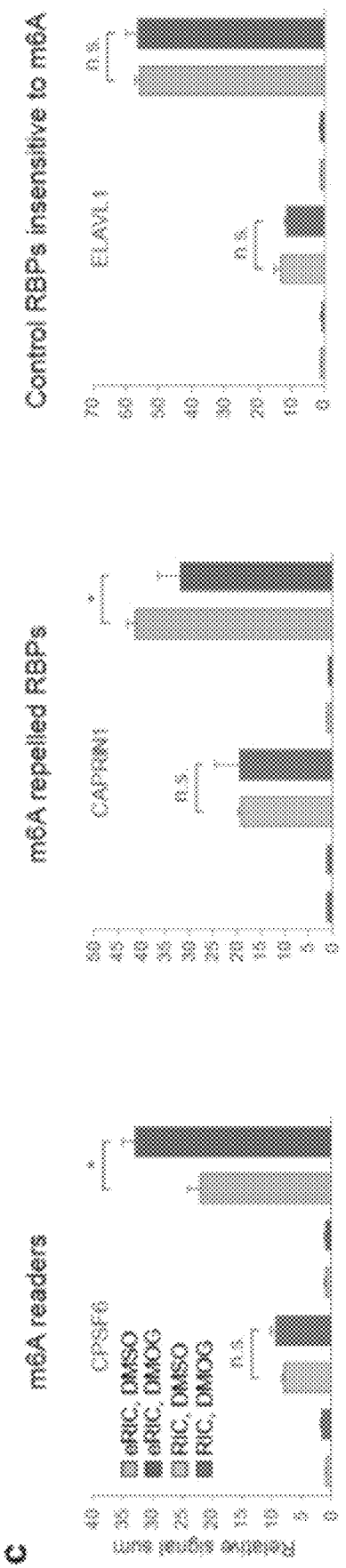
FIG. 13A
FIG. 13B
FIG. 13C - Part 1

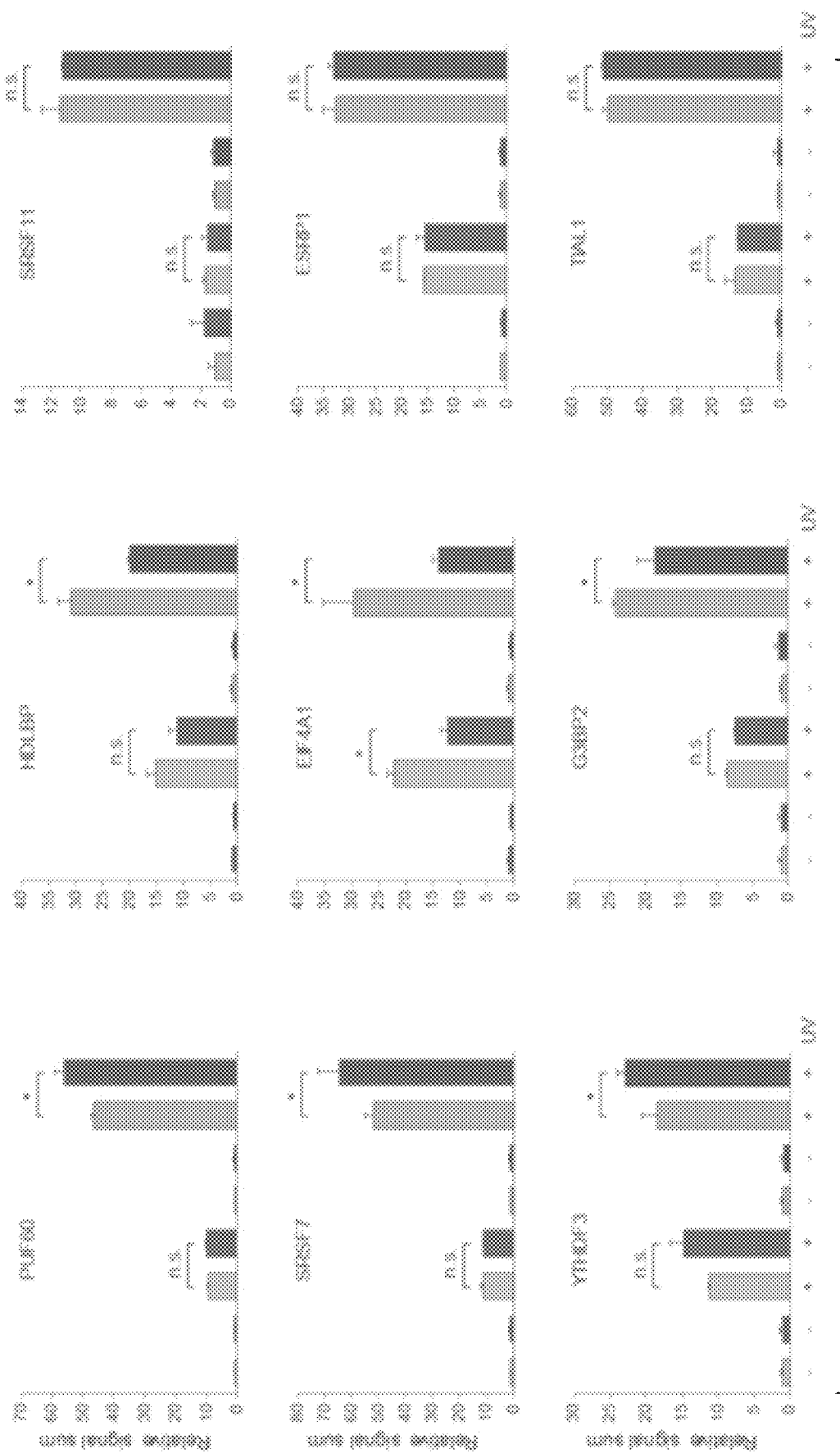
FIG. 13C – Part 2

SEQUENCE LISTING

```
<160> NUMBER OF SEQ ID NOS: 25

<210> SEQ ID NO 1
<211> LENGTH: 22
<212> TYPE: DNA
<213> ORGANISM: Homo sapiens

<400> SEQUENCE: 1
tggagattgt tgccatcaac ga                                            22

<210> SEQ ID NO 2
<211> LENGTH: 21
<212> TYPE: DNA
<213> ORGANISM: Homo sapiens

<400> SEQUENCE: 2
cccattctcg gccttgactg t                                             21

<210> SEQ ID NO 3
```

```
<211> LENGTH: 20
<212> TYPE: DNA
<213> ORGANISM: Homo sapiens

<400> SEQUENCE: 3
tcaccggagt ccatcacgat                                            20

<210> SEQ ID NO 4
<211> LENGTH: 20
<212> TYPE: DNA
<213> ORGANISM: Homo sapiens

<400> SEQUENCE: 4
cgcgagaaga tgacccagat                                            20

<210> SEQ ID NO 5
<211> LENGTH: 25
<212> TYPE: DNA
<213> ORGANISM: Homo sapiens

<400> SEQUENCE: 5
ttaccctact gatgatgtgt tgttg                                      25

<210> SEQ ID NO 6
<211> LENGTH: 18
<212> TYPE: DNA
<213> ORGANISM: Homo sapiens

<400> SEQUENCE: 6
cctgcggttc ctctcgta                                              18

<210> SEQ ID NO 7
<211> LENGTH: 23
<212> TYPE: DNA
<213> ORGANISM: Homo sapiens

<400> SEQUENCE: 7
gaaactgcga atggctcatt aaa                                        23

<210> SEQ ID NO 8
<211> LENGTH: 23
<212> TYPE: DNA
<213> ORGANISM: Homo sapiens

<400> SEQUENCE: 8
cacagttatc caagtgggag agg                                        23

<210> SEQ ID NO 9
<211> LENGTH: 20
<212> TYPE: DNA
<213> ORGANISM: Homo sapiens

<400> SEQUENCE: 9
ggccatacca ccctgaacgc                                            20

<210> SEQ ID NO 10
<211> LENGTH: 20
<212> TYPE: DNA
<213> ORGANISM: Homo sapiens

<400> SEQUENCE: 10
cagcacccgg tattcccagc                                            20
```

```
<210> SEQ ID NO 11
<211> LENGTH: 20
<212> TYPE: DNA
<213> ORGANISM: Homo sapiens

<400> SEQUENCE: 11
tcgctgcgat ctattgaaag                                                  20

<210> SEQ ID NO 12
<211> LENGTH: 20
<212> TYPE: DNA
<213> ORGANISM: Homo sapiens

<400> SEQUENCE: 12
aggaagacga acggaaggac                                                  20

<210> SEQ ID NO 13
<211> LENGTH: 20
<212> TYPE: DNA
<213> ORGANISM: Homo sapiens

<400> SEQUENCE: 13
tgaaaaccgg cacaagacag                                                  20

<210> SEQ ID NO 14
<211> LENGTH: 20
<212> TYPE: DNA
<213> ORGANISM: Homo sapiens

<400> SEQUENCE: 14
ctggccagaa cttccaacac                                                  20

<210> SEQ ID NO 15
<211> LENGTH: 20
<212> TYPE: DNA
<213> ORGANISM: Homo sapiens

<400> SEQUENCE: 15
accccctagg aatcacctcc                                                  20

<210> SEQ ID NO 16
<211> LENGTH: 20
<212> TYPE: DNA
<213> ORGANISM: Homo sapiens

<400> SEQUENCE: 16
gcctaggagg tctggtgaga                                                  20

<210> SEQ ID NO 17
<211> LENGTH: 21
<212> TYPE: DNA
<213> ORGANISM: Homo sapiens

<400> SEQUENCE: 17
ctgtgacctg cagctcatcc t                                                21

<210> SEQ ID NO 18
<211> LENGTH: 26
<212> TYPE: DNA
<213> ORGANISM: Homo sapiens

<400> SEQUENCE: 18
taagttctct gacgttgact gatgtg                                           26
```

```
<210> SEQ ID NO 19
<211> LENGTH: 23
<212> TYPE: DNA
<213> ORGANISM: Homo sapiens

<400> SEQUENCE: 19
gtgagaagat ggatgttgag ttg                                              23

<210> SEQ ID NO 20
<211> LENGTH: 20
<212> TYPE: DNA
<213> ORGANISM: Homo sapiens

<400> SEQUENCE: 20
gatagcagca cggtatgagc                                                  20

<210> SEQ ID NO 21
<211> LENGTH: 20
<212> TYPE: DNA
<213> ORGANISM: Homo sapiens

<400> SEQUENCE: 21
tgaagtggac gatgaacgca                                                  20

<210> SEQ ID NO 22
<211> LENGTH: 20
<212> TYPE: DNA
<213> ORGANISM: Homo sapiens

<400> SEQUENCE: 22
ccattcttca cccagagcgt                                                  20

<210> SEQ ID NO 23
<211> LENGTH: 20
<212> TYPE: DNA
<213> ORGANISM: Homo sapiens

<400> SEQUENCE: 23
ccaggctcac ctcactaacc                                                  20

<210> SEQ ID NO 24
<211> LENGTH: 20
<212> TYPE: DNA
<213> ORGANISM: Homo sapiens

<400> SEQUENCE: 24
ctggctggta ggggttgatt                                                  20

<210> SEQ ID NO 25
<211> LENGTH: 23
<212> TYPE: DNA
<213> ORGANISM: Homo sapiens

<400> SEQUENCE: 25
gtggagattg ttgccatcaa cga                                              23
```

ENHANCED RNA INTERACTOME CAPTURE (eRIC)

CROSS REFERENCE TO RELATED APPLICATIONS

This application is a National Stage Application of International Application Number PCT/EP2018/072348, filed Aug. 17, 2018; which claims priority to European Application No. 17186948.0, filed Aug. 18, 2017.

The Sequence Listing for this application is labeled "SeqList-05Feb20-ST25.txt", which was created on Feb. 5, 2020 and is 4 KB. The entire content is incorporated herein by reference in its entirety.

The present invention relates to an improved method of detecting RNA-binding proteins (RBPs) in a cell, tissue or organism, comprising the use of oligonucleotides that comprise locked nucleic acid (LNA)-nucleotide analogues in the sequence thereof.

BACKGROUND OF THE INVENTION

RNA-binding proteins (RBPs) associate with RNAs from synthesis to decay forming dynamic complexes called ribonucleoproteins (RNPs). RBPs control RNA fate and thus play central roles in gene expression. The implementation of technologies such as immunoprecipitation combined with microarrays or next generation sequencing have allowed the deeper study of RNA networks controlled by individual RBPs. However, the scope of proteins involved in RNA biology is still unclear and appears to have been previously underestimated, as judged by the mRNA interactome of HeLa and HEK293 cells.

A number of approaches have been previously used to study the RNA interactome, i.e. the collective of RNA-binding proteins. Genome-wide protoarrays and fluorescent RNA probes were used in two different studies to systematically identify yeast RBPs (Scherrer, T., Mittal, N., Janga, S. C. & Gerber, A. P. A screen for RNA-binding proteins in yeast indicates dual functions for many enzymes. PLoS One 5, e15499 (2010); Tsvetanova, N. G., Klass, D. M., Salzman, J. & Brown, P. O. Proteome-wide search reveals unexpected RNA-binding proteins in Saccharomyces cerevisiae. PLoS One 5 (2010)). Immobilized RNA probes were also employed as bait to capture specific RBPs in vitro followed by quantitative mass spectrometry (Butter, F., Scheibe, M., Morl, M. & Mann, M. Unbiased RNA-protein interaction screen by quantitative proteomics. Proc Natl Acad Sci U S A 106, 10626-10631 (2009)).

However, these approaches do not discriminate non-physiological RNA-protein interactions, facilitated by the biochemical properties of the respective polypeptides, from those taking place in living cells. In silico algorithms have been used to identify candidate RBPs, searching for RNA-binding domains (RBDs) or RNA-related enzymatic activities (Anantharaman, V., Koonin, E. V. & Aravind, L. Comparative genomics and evolution of proteins involved in RNA metabolism. Nucleic Acids Res 30, 1427-1464 (2002)) in the cellular proteome. These approaches identified additional proteins as potential RBPs that share similar structural and functional features with previously known RNA binders.

However, unconventional RBPs cannot be identified by these analyses, as illustrated by the recently published RNA interactome datasets (Baltz, A. G. et al. The mRNA-Bound Proteome and Its Global Occupancy Profile on Protein-Coding Transcripts. Mol Cell 46, 674-690 (2012); Castello, A. et al. Insights into RNA Biology from an Atlas of Mammalian mRNA-Binding Proteins. Cell 149, 1393-1406 (2012)).

US 2013-123123 discloses a method comprising: a) cross-linking the contents of a cell using a heat stable crosslinking agent to produce cross-linked ribonucleotide complexes; b) fragmenting the cross-linked ribonucleotide complexes to produce complexes comprising protein, RNA fragments and, optionally, genomic DNA fragments; c) contacting the complexes with a plurality of non-overlapping oligonucleotides comprising an affinity tag and that are complementary to a specific target RNA of the cell under high stringency conditions that include high temperature; d) isolating complexes that contain the oligonucleotides using the affinity tag to produce isolated complexes; e) enzymatically releasing the protein, RNA fragments and/or the genomic DNA fragments from the isolated complexes to produce a released component, without reversing the crosslinking; and f) analyzing the released component.

WO 2015/191780 relates to the zinc-finger protein CCCTC-binding factor (CTCF) RNA interactome. WO 2016/149455 relates to polycomb-associated RNAs, libraries and fragments of those RNAs, inhibitory nucleic acids and methods and compositions for targeting RNAs, and methods of use thereof WO 2009/024781 discloses methods for isolating polypeptides and polypeptide complexes that are associated with a target nucleic acid sequence are provided. The methods comprise the steps of obtaining a sample that comprises a target nucleic acid sequence and one or more polypeptides associated with that target nucleic acid sequence; contacting the sample with at least one oligonucleotide probe that comprises a sequence that is complimentary to and capable of hybridising with at least a portion of the target nucleic acid sequence, wherein the oligonucleotide probe comprises at least one locked nucleic acid (LNA) nucleotide and wherein the oligonucleotide probe further comprises at least one affinity label; allowing the at least one oligonucleotide probe and the target nucleic acid sequence to hybridise with each other so as to form a probe-target hybrid; isolating the probe-target hybrid from the sample by immobilizing the probe-target hybrid through a molecule that binds to the at least one affinity label; and eluting the one or more polypeptides that are associated with the target nucleic acid sequence. Probes for use in the methods of screening are also provided.

U.S. Pat. No. 8,748,354 discloses a method of RNA interactome analysis comprising: a) cross-linking the contents of a cell using a heat stable crosslinking agent to produce cross-linked ribonucleotide complexes; b) fragmenting the cross-linked ribonucleotide complexes to produce complexes comprising protein, RNA fragments and, optionally, genomic DNA fragments; c) contacting the complexes with a plurality of non-overlapping oligonucleotides comprise an affinity tag and that are complementary to a specific target RNA of the cell under high stringency conditions that include high temperature; d) isolating complexes that contain the oligonucleotides using the affinity tag to produce isolated complexes; e) enzymatically releasing the protein, RNA fragments and/or the genomic DNA fragments from the isolated complexes to produce a released component, without reversing the crosslinking; and f) analysing the released component.

Rogell et al. (in: Rogell et al. "Specific RNP capture with antisense LNA/DNA mixmers", RNA, vol. 23, no. 8, 5 May 2017, pages 1290-1302 discloses "specific ribonucleoprotein (RNP) capture," a method for the determination of the proteins bound to specific transcripts in vitro and in cellular systems. Specific RNP capture uses UV irradiation to covalently stabilize protein-RNA interactions taking place at "zero distance." Proteins bound to the target RNA are then captured by hybridization with antisense locked nucleic acid (LNA)/DNA oligonucleotides covalently coupled to a magnetic resin. After stringent washing, interacting proteins are identified by quantitative mass spectrometry. The method revealed previously unknown rRNA-binding proteins.

Beckmann (in: Benedikt M. Beckmann: "RNA interactome capture in yeast", Methods, vol. 118-119, 2016, pages 82-92, discloses a yeast RNA interactome capture protocol which employs RNA labeling, covalent UV crosslinking of RNA and proteins at 365nm wavelength (photoactivatable-ribonucleoside-enhanced crosslinking, PAR-CL) and finally purification of the protein-bound mRNA.

Conrad et al. (in: Conrad et al. "Serial interactome capture of the human cell nucleus", Nature Comm., vol. 7, 4 April 2016, pages 1-11) disclose 'serial RNA interactome capture' (serIC), a multiple purification procedure of ultraviolet-crosslinked poly(A)-RNA-protein complexes that enables global RBP detection.

A recently developed method (System-wide identification of RNA-binding proteins by interactome capture. Castello A, Horos R, Strein C, Fischer B, Eichelbaum K, Steinmetz L M, Krijgsveld J, Hentze M W. Nat Protoc. 2013 Mar;8 (3):491-500) improved the situation, but still methods are required that provide satisfactory results.

According to a first aspect thereof, the above object is solved by a method of detecting RNA-binding proteins (RBPs) in a cell, comprising the steps of: a) covalently cross-linking the contents of cells, tissues or organisms comprising RBPs using suitable irradiation to produce cross-linked ribonucleotide complexes; b) lysing said material comprising said cross-linked ribonucleotide complexes; c) contacting said cross-linked ribonucleotide complexes under suitable conditions at temperatures above 0° C., preferably at at least 15° C. and above with at least one oligonucleotide that is complementary to at least one specific target RNA of said cell, wherein said oligonucleotide comprises at least one locked nucleic acid (LNA)-nucleotide analogue in the sequence thereof, and wherein said oligonucleotide is coupled to a solid support; d) isolating complexes that comprise said at least one oligonucleotide using said solid support; e) enzymatically releasing said RBPs from said isolated complexes to produce released RBPs; and f) analyzing said released RBPs. The method is usually performed in vitro, e.g. using isolated cells and/or tissues, e.g. is applied to cells or tissues derived from an organism to identify the protein-RNA interactions that occur in vivo.

The inventors developed a modified protocol based on RNA Interactome Capture for the unbiased identification of the proteins that interact with poly(A) RNAs in vivo. The use of locked nucleic acid (LNA) nucleotide analogues allows modifications of the protocol (including more stringent capture and wash conditions, and a more specific elution) in comparison with its precedent method. The LNA-based interactome capture leads to a profound reduction of contaminations, including genomic DNA and non polyadenylated RNAs. The inventive new protocol has been successfully applied to cell types in which the previous method underperforms, and provides significant advantages for comparative analyses under different experimental conditions.

Advantageously, the inventive method comprises the utilization of oligo(dT) probes in which some of the bases are substituted with a locked nucleic acid (LNA). LNA-T displays higher affinity for complementary poly(A) tracts and permits the application of more stringent conditions, reducing contamination without compromising or even enhancing capture of poly(A) RNA.

Furthermore, by incorporating, for example, an LNA-T at every other position of a 20-mer (LNA2.T), the inventors have been able to perform the entire protocol, including capture and all washes, at about 37-40° C. instead of 4° C. as in the previous version of the technique.

In addition, the inventors have included a highly stringent pre-elution step in, preferably pure (e.g. bidest, tridest), water at about 40° C., so contaminant nucleic acids or proteins with less affinity for the LNA probe or that interact unspecifically with the solid support (e.g. magnetic beads) will be eluted. A pre-elution of this kind would not be compatible with classic oligo (e.g. oligo(dT)) probes.

The increased temperature along the protocol combined with the added pre-elution step leads to a profound reduction of the contamination with genomic DNA and non-polyadenylated RNAs when compared with the previous protocol.

Finally, elution now is achieved by RNase digestion and/or heat elution that is specific for RNA-bound material, which is conducted under an identical or lower temperature that the one that was employed all along the earlier protocol, and under less stringent salt conditions, ensuring that contaminant proteins that may remain are not co-eluted.

In summary, in view of the above, it was found that the new method leads to reduced levels of contaminant proteins, identifying more RBPs and increasing the reliability of the identified proteins in comparison to earlier methods.

Preferred is the method according to the present invention, wherein said irradiation is selected from UV light, such as, for example of about 254 nm or about 365 nm.

In the context of the present invention, the term "about" shall mean a variation of +/−10% of a given value, unless indicated otherwise.

In the context of the method according to the present invention, the cells are lysed under denaturing conditions. Such conditions are known from the literature, e.g. as cited herein, and the state of the art. Preferred are buffers comprising about 500 mM lithium chloride and about 0.5% lithium dodecyl sulphate.

Further preferred is the method according to the present invention, further comprising a step of shearing genomic DNA before isolating said complexes. Shearing can be done as known in the art, for example, samples are passed 3-5 and then 5-10 times through syringes with 22G (gauge 0.7 mm diameter) and 27G needles (gauge 0.4 mm diameter), respectively.

With the aim to reduce protein-protein interactions that may survive the capture conditions, the inventors further include an optional incubation at about 60° C. for about 10-15 min after lysis and shearing treatments. This step is followed by centrifugation (about 230-500×g for about 3-5 min at about 4° C.) to remove insoluble material, for example presumably fragments of genomic DNA and membranous structures that contaminated the samples in the previous protocol, thus compromising its quality.

Preferably, according to the method according to the present invention, said contacting step c) is performed at about 37 to about 40° C. The inventors have successfully purified poly(A) RNAs when executing the entire protocol, including capture and all washes, at 37-40° C. instead of 4° C. (cold room) as in the previous version of the technique.

Particularly preferred is the method according to the present invention, further comprising a stringent pre-elution in water at about 40° C., preferably for about 5 to about 10 min. The high stability of the LNA oligo-poly(A) RNA duplex allows the incorporating of a highly stringent pre-elution step in pure water at 40° C. Lowering salt concentration decreases the stability of RNA-DNA and RNA-RNA duplexes, so contaminant nucleic acids with less affinity for the LNA probe are eluted. It is important to note that a pre-elution of this kind would not be compatible with classic oligo(dT) probes.

Preferred is the method according to the present invention wherein said oligonucleotide elution is specific for RNA-bound material and is performed at the identical or lower temperature that the one that was used for the steps of the method before, and under less stringent salt conditions, whereby it is ensured that potential contaminant proteins are not co-eluted.

Preferred is the method according to the present invention, wherein said RBPs are released by suitable enzymatic digestion, preferably suitable RNA digestion according to methods in the art. Preferred are RNases A and/or T1. In order to increase the specificity of the elution and decrease the chances of co-eluting contaminants, the inventors substituted the heat elution by an RNase based elution at about 37° C. (for about 30-60 min) that is specific for RNA-bound material.

The method according to the present invention further optionally comprises the step of centrifugation and/or vacuum concentrating, preferably vacuum concentrating, the RBP samples. This increases sample recovery upon concentration to virtually 100%.

Finally, the method according to the present invention comprises analyzing said released RBPs. Said analyzing can comprise a preparation using Single-Pot Solid-Phase-enhanced Sample Preparation (SP3), sequencing, and quantitative mass spectrometry. SP3 is disclosed, for example, in Hughes CS et al., Ultrasensitive proteome analysis using paramagnetic bead technology. Mol Syst Biol. 2014 Oct 30;10:757, or WO 2015/118152. The ribonucleotide complexes comprise RNA and proteins, the proteins in the ribonucleotide complexes may be analysed, e.g., by immunoblotting or mass spectrometry, the RNA may be analysed using heat elution and, e.g., sequencing or using PCR. Methods are known to the person of skill, and described in the art, for example in Marchese D., et al., Advances in the characterization of RNA-binding proteins. Wiley Interdiscip Rev RNA. 2016 Nov;7(6):793-810.

The target RNA to which the oligonucleotides hybridize may vary greatly. In preferred cases, the oligonucleotides hybridize to poly(A) RNA, which includes mRNAs and long non-coding RNAs.

According to the present invention, "high stringency conditions" are used in different steps of the method, like hybridization and washing steps. High stringency conditions as used herein refer to conditions that are compatible to produce binding pairs of nucleic acids, e.g., probes and targets, of sufficient complementarity while being incompatible to the formation of binding pairs between binding members of insufficient complementarity to provide for the desired specificity. In certain cases "high stringency" includes incubation with high-salt buffers, e.g. with 500 mM LiCl, and 0.1-0.5% (w/v) LiDS. The conditions used should be sufficient to allow high stringency hybridization of the oligonucleotides to the RNA target, but not reversal of the crosslinking of the sample. As an example, captured complexes are washed at about 37-40° C., once with lysis buffer and twice with each of the buffers 1, 2 and 3 (see below). The magnetized beads are then subjected to a stringent pre-elution in pure water at 40° C. for about 5-10 min. In another aspect, highly stringent conditions comprise low salt conditions (e.g. pure water) at temperatures of, e.g. about 40° C., in order to destabilize undesired RNA-DNA and RNA-RNA duplexes, and RNA/DNA unespecific interactions with the solid suport (e.g. magnetic beads), so that contaminant nucleic acids will be eluted. Since the interaction of poly(A) tracts and LNA-containing probes was shown to be stable under conditions that are even more stringent, the present invention also includes use of high, e.g. about 3-5 M, or 4 M guanidine thiocyanate-containing buffers.

Preferred is the method according to the present invention, wherein said oligonucleotide has a length of between 15 to 25 bases, preferably 20 bases. LNA oligo(T) capture probes can be synthesized and used with other lengths and with varying degrees of LNA substitution. Substitution of a DNA oligo(dT)20 oligonucleotide with LNA-T results in significantly increased thermal duplex stabilities in all LNA oligo(T) designs, corresponding to an increase in melting temperature ranging from +2.8 to +6.0° C. per LNA thymidine monomer. A fully substituted LNA-T20 would have a TM of above 95° C., i.e. with an exceptionally high thermal stability. By comparison, for example the oligo LNA2.T as described herein shows a TM of 77° C. and thus an increase of 37° C. compared to an all-DNA reference and/or control probe. Preferred is therefore the method according to the present invention, wherein said oligonucleotide comprises an LNA at every other position of said oligomer, such as, for example, an LNA-T. The present invention also contemplates the use of oligo(T) probes containing different ratios of LNA thymidines.

In another aspect of the present invention, the method according to the present invention further comprises the detection of changes in the RNA-association of the RBPs as detected, when compared with a control sample or a sample obtained under different experimental conditions. Hence, in certain embodiments, the interaction profiles for an RNA in two or more different samples may be obtained using the above methods, and compared. In these embodiments, the results obtained from the above-described methods may be normalized, e.g., to a control RNA, and compared.

This may be done by comparing ratios, or by any other means. In particular embodiments, the interaction profiles of two or more different samples may be compared to identify interactions that are associated with a particular disease or condition (e.g., an interaction that is induced by the disease or condition and therefore may be part of a pathway implicated in that disease or condition). The different samples may consist of an "experimental" sample, i.e., a sample of interest, and a "control" sample to which the experimental sample may be compared.

The inventive method can be employed in a variety of diagnostic, drug discovery, and research applications that include, but are not limited to, diagnosis or monitoring of a disease or condition (where the profile of the interactions of an RNA provides a marker for the disease or condition), discovery of drug targets (where a particular profile is differentially present in a disease or condition and may be targeted for drug therapy), drug screening (where the effects of a drug are monitored by assessing a profile of interactions), determining drug susceptibility (where drug susceptibility is associated with a particular profile of interactions) and basic research (where is it desirable to identify the interactions with an RNA in a particular sample, or, in certain embodiments, the relative levels of a particular interactions in two or more samples).

Yet another aspect of the present invention then relates to a kit comprising materials for performing the method according to the present invention, for example at least one suitable oligonucleotide that is complementary to at least one specific target RNA of said cell and comprises at least one locked nucleic acid (LNA)-nucleotide, buffers, reagents, and/or instructions for use.

Yet another aspect of the present invention then relates to the use of the kit according to the present invention for detecting RNA-binding proteins (RBPs) in a cell, e.g. in the context of the detection of changes in the RNA-association of the RBPs as described above.

Although the previous version of RNA interactome capture has been successfully applied to several cellular models, the inventors have observed that it does not perform appropriately for quite a number of different cell types, displaying relatively high levels of contaminants such as genomic DNA and non polyadenylated RNAs. The co-purification of these contaminants together with their associated proteins compromises the quality and interpretation of the data.

Underperformance of the previous technique has been particularly evident when employing cells of relatively small volume, as for instance leukocytes and leukemia cells (which can be around 20 times smaller than HeLa cells, for which RNA interactome capture was originally developed). In contrast to the previous version, the inventive enhanced RNA interactome capture protocol has proven to be successful even when applied to challenging cell types (including the ones mentioned above), providing cleaner outcomes highly depleted of contaminant DNA/non-poly(A) RNA and their associated proteins.

In more detail, the inventors' method is based on RNA interactome capture, which allows the unbiased identification of the cellular RNA-bound proteome. In the previous technique, RNA-binding proteins (RBPs) are covalently crosslinked to RNA in vivo through the irradiation of cells with 0.15 J cm$^{-2}$ of 254 nm or 365 nm (PAR-CL) UV light. Subsequently, cells are lysed under denaturing conditions, and the ribonucleoprotein complexes are purified using oligo(dT) coupled to magnetic beads. Captured complexes are subjected to successive rounds of stringent washes, and heat eluted (50-55° C. for 5 min). Proteins are then released by RNase digestion, concentrated using Amicon ultra centrifugal filters (e.g. Millipore) and finally identified by quantitative mass spectrometry.

The inventive method "enhanced RNA interactome capture" is based on the utilization of oligo(dT) probes in which some of the bases are substituted with a type of nucleotide analogue called locked nucleic acid (LNA). LNA-T display higher affinity for complementary poly(A) tracts and permit the application of more stringent conditions, reducing contamination without compromising or even enhancing capture of poly(A) RNA.

By incorporating, for example, an LNA-T at every other position of a 20-mer (LNA2.T), the inventors have been able to successfully purify poly(A) RNAs when executing the entire protocol, including capture and all washes, at 37-40° C. instead of 4° C. as in the previous technique.

In addition, the inventors have exploited the high stability of the LNA2.T- poly(A) RNA duplex by incorporating a highly stringent pre-elution step in pure water at 40° C. (Lowering salt concentration decreases stability of RNA-DNA and RNA-RNA duplexes, so contaminant nucleic acids with less affinity for the LNA2.T probe are eluted here). It is important to note that a pre-elution of this kind would not be compatible with classic oligo(dT) probes. The increased temperature along the protocol combined with the added pre-elution step leads to a profound reduction of hundreds of times on the contamination with genomic DNA and non-polyadenylated RNAs such as the 28S and 18S rRNA, in comparison with the previous protocol.

In the previous version of RNA interactome capture, capture and washes were performed at 4° C., while elution was carry out at 50-55° C. This abrupt increase in temperature potentially causes the co-elution of contaminants (including proteins unespecifically associated with the beads employed for the pull down). In order to increase the specificity of the elution and decrease the chances of co-eluting contaminants, the inventors substitute the heat elution by an RNase-based elution at about 37° C. (for about 30-60 min). Thus, elution now is achieved under an identical or lower temperature that the one that was employed all along the protocol before, and under less stringent salt conditions, ensuring that contaminant proteins are not co-eluted. Moreover, since RNase-mediated elution is specific for RNA-bound material, it avoids the problems of eluting contaminants associated with the bead matrix by a biophysical method like elevated temperature.

In the inventors' new protocol, proteins samples are preferably vacuum concentrated using a SpeedVac. Using the Amicon ultra centrifugal filters (Millipore) previously employed may be still suitable, but is commonly associated with protein loss. Thus, the new protocol increases sample recovery upon concentration to virtually 100%.

Although the previous version of RNA interactome capture has been successfully applied to diverse cellular models, the inventors and others have observed that it does not perform appropriately for a number of different cell types, displaying relatively high levels of contaminants such as genomic DNA and non polyadenylated RNAs. The co-purification of these contaminants together with their associated proteins can compromise the quality and interpretation of the data. Underperformance of the previous technique has been particularly evident when employing cells of relatively small volume, as for instance leukocytes and leukemia cells (which can be around 20 times smaller than HeLa cells, for which RNA interactome capture was originally developed). In contrast to the previous version, the new Enhanced RNA interactome capture protocol has proven to be successful even when applied to challenging cell types (including the ones mentioned above), providing cleaner outcomes highly depleted of contaminant DNA/non-poly(A) RNA and their associated proteins.

Due to the higher stringency of the capture/washes and higher specificity of the elution, contaminant proteins are significantly reduced in the method according to the invention. In order to be considered as a hit in an interactome capture assay, a protein is usually required to be enriched in the crosslinked sample in relation to a control that is not crosslinked but otherwise treated identically (noCL). By reducing the levels of contaminant proteins in noCL controls, LNA-based interactome leads to the identification of more confident RBPs and a higher number of RBPs, and facilitates the identification of changes on the RNA-association of those proteins under different experimental conditions, an approach that the inventors term 'comparative RNA interactome capture'.

The present invention is particularly useful in so-called "discovery applications" (e.g. target identification, study of drug effects, etc., see also above) where a high degree of sensitivity and low background levels are essential.

Preferred features of each aspect of the invention are as for each of the other aspects mutatis mutandis. The prior art documents mentioned herein are incorporated to the fullest extent permitted by law. Although the present invention and its advantages have been described in detail, it should be understood that various changes, substitutions and alterations can be made herein without departing from the spirit and scope of the invention as defined in the appended claims. The present invention will be further illustrated in the following Examples which are given for illustration purposes only and are not intended to limit the invention in any way.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

```
                                    (SEQ ID NO: 1)
GAPDH Fw:        TGGAGATTGTTGCCATCAACGA;

(SEQ ID NO: 2)
GAPDH Rv:        CCCATTCTCGGCCTTGACTGT;

(SEQ ID NO: 3)
betaActin Fw:    TCACCGGAGTCCATCACGAT;
and (SEQ ID NO: 4)
betaActin Rv:    CGCGAGAAGATGACCCAGAT.
```

Figure 1:
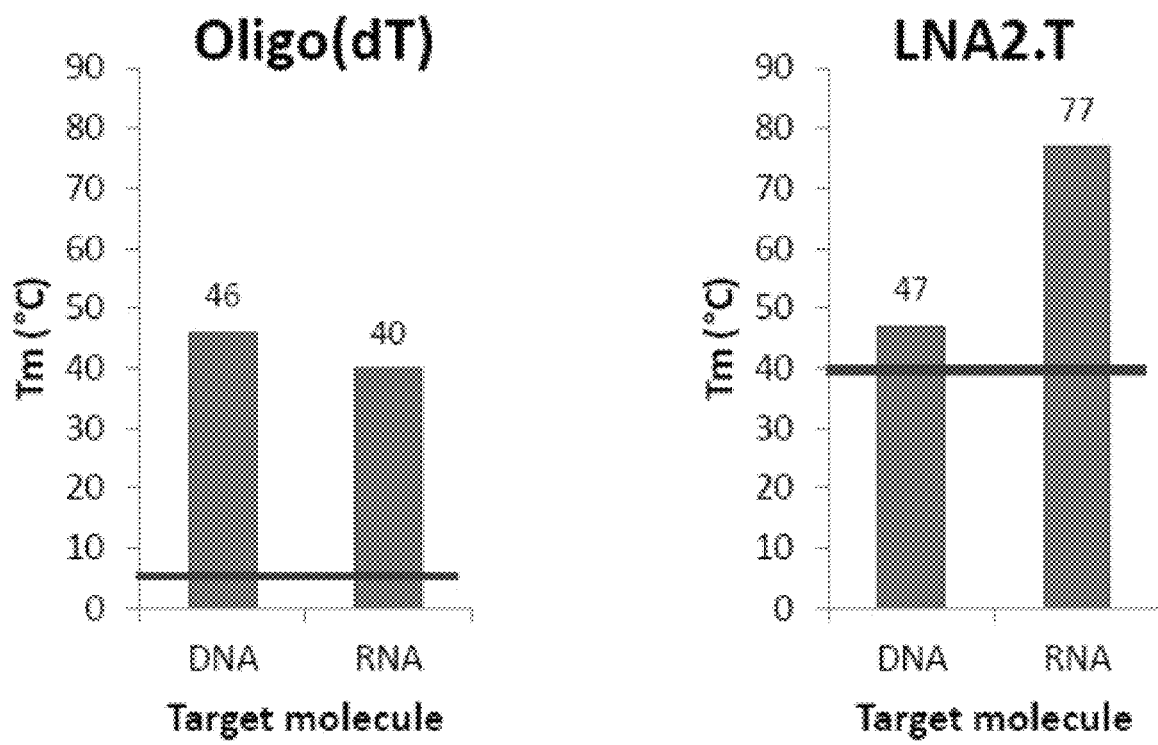
FIG. 1 shows a comparison of melting temperatures of a regular dT 20mer oligonucleotide when hybridized to its target DNA or RNA sequence, compared to the LNA oligo as depicted. (A) Scheme of the LNA2.T probed used in enhanced interactome capture. Black and red T represent DNA and LNA thymine bases, respectively. The employed 5AmMC6 flexible linker is also depicted. (B) Comparison of the predicted melting temperatures (Tm) of LNA2.T and a standard DNA oligonucleotide of the same length, when complexed with DNA and RNA complementary strands. LNA2.T-RNA duplexes remain stable at much higher temperatures (Tm=77° C. vs 40° C.). LNA2.T also exhibits a greater melting temperature difference between intended —RNA and undesirable —DNA duplexes (delta Tm=+30° C. vs −6° C.). Horizontal red lines represents capture and wash temperatures employed in the previous method (4° C.) vs enhancedinteractome capture (37-40° C.). $T_m$ were calculated with the ad-hoc tool provided by Exiqon (www.exiqon.com). A salt concentration (Na+) of 115 mM and a neutral pH (pH 7-8) were assumed.
Figure 2:
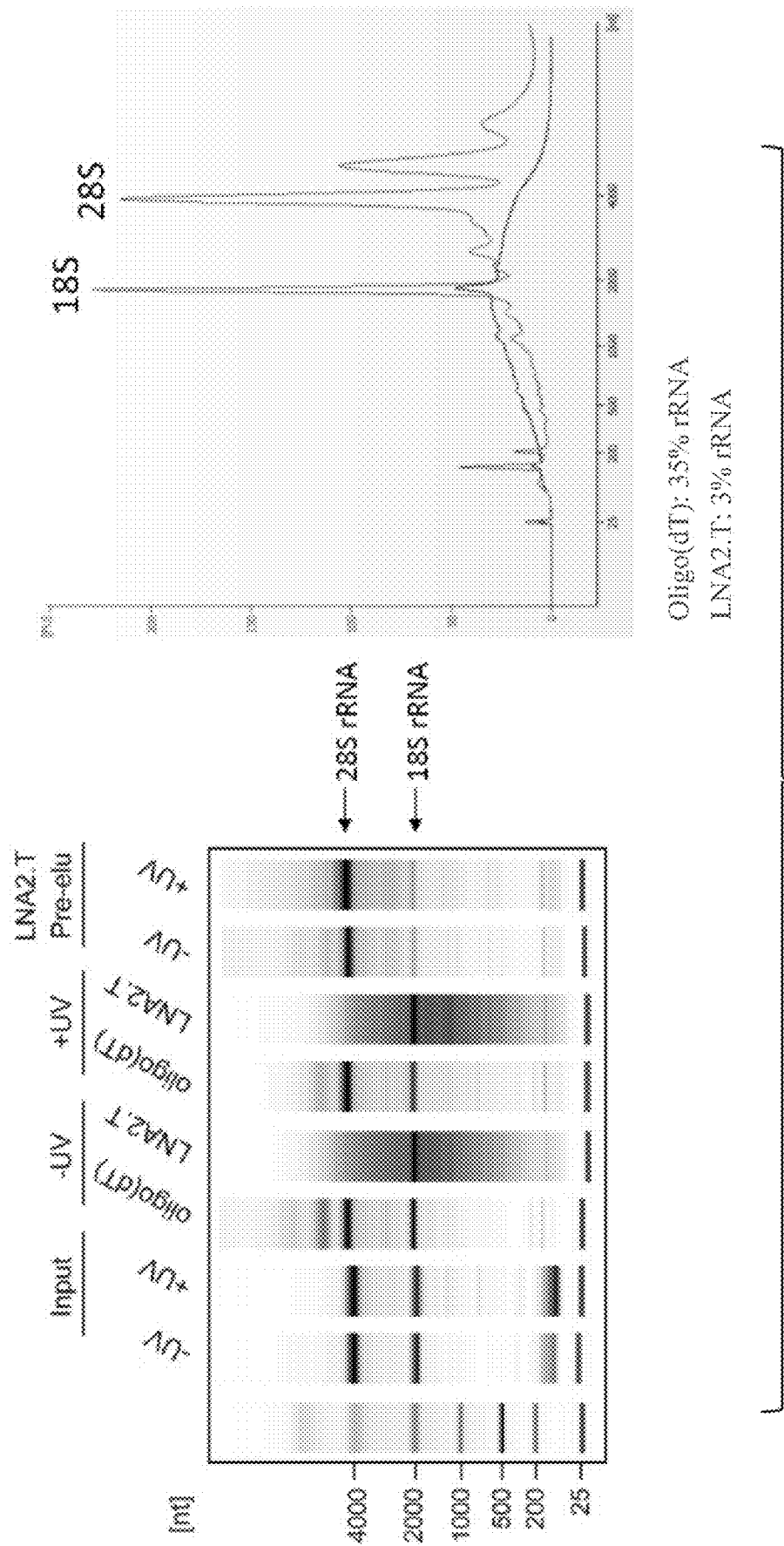
FIG. 2 shows the analysis of the RNA captured by enhanced interactome capture. Eluates obtained by previous method (oligo(dT)) or enhanced interactome capture (LNA2.T) were analyzed using a 6000 Pico bioanalyzer. Enhanced interactome capture leads to reduced amounts of the non poly(A) (and highly abundant) RNAs 18S and 28S rRNAs while it leads to higher levels of RNAs on the size-range expected for mRNAs. Note that the pre-elution step (pre-elu) with pure water incorporated in the enhanced interactome capture leads to an effective elution of rRNAs, specially the 28S rRNA, without compromising capture of poly(A) RNAs. On the right panel a representative electropherogram is shown. The fraction of rRNAs vs total RNA on eluates is reduced from approximately 35% to approximately 3% by enhanced interactome capture.
Figure 3:
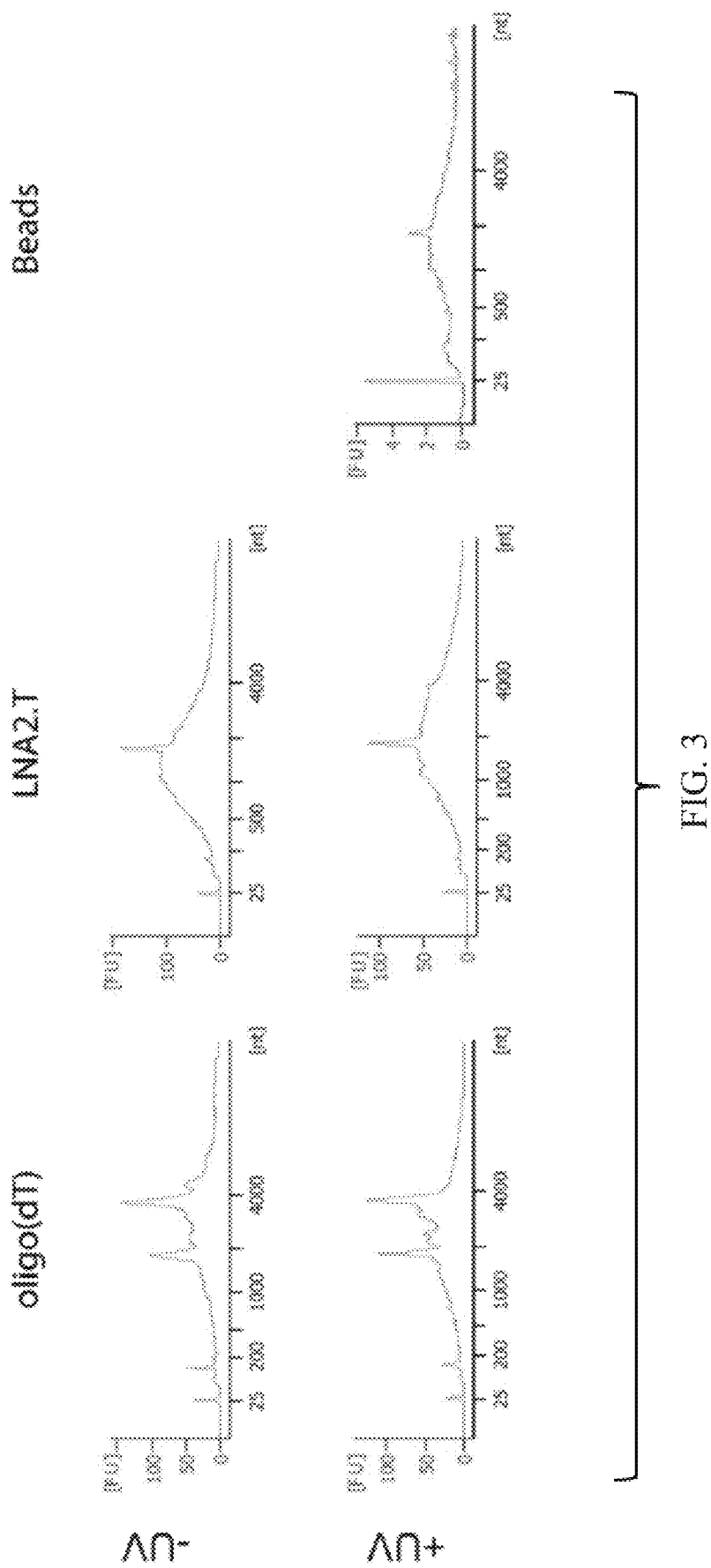
FIG. 3 shows the analysis of the RNA captured by enhanced interactome capture. Representative electropherograms of eluates obtained by previous method (oligo(dT)) or enhanced interactome capture (LNA2.T) were analyzed using a 6000 Pico bioanalyzer. Samples were also incubated with same beads used for LNA2.T but that were not coupled to any oligo, and subjected otherwise to the enhanced interactome capture protocol (Beads). No significant amount of RNA is captured with the uncoupled beads, demonstrating that pull down of RNA by enhanced interactome capture is achieved through interaction with the LNA2.T probe and not by unspecific interaction to the solid support. Note smaller scale on "beads" electropherogram.
Figure 4:
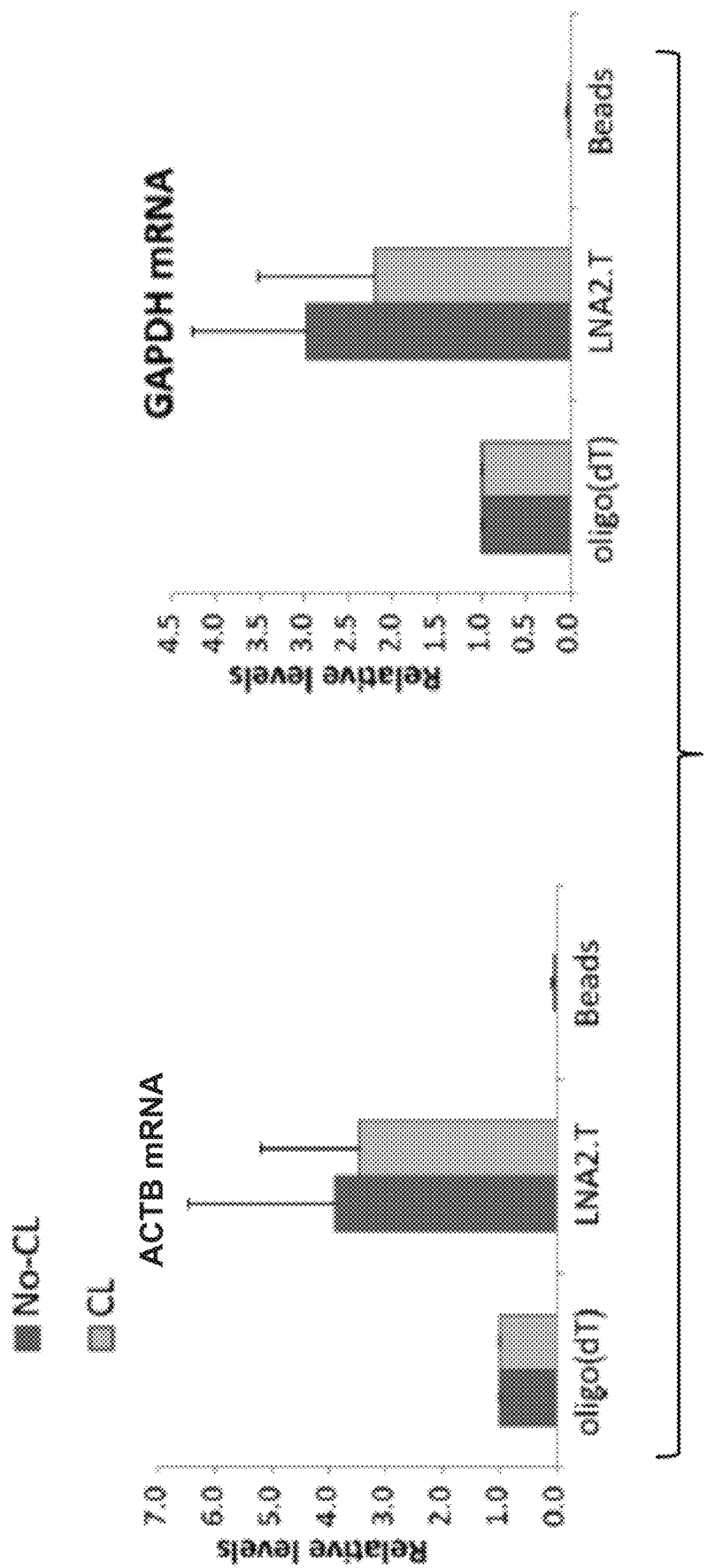
FIG. 4 shows an effective capture of poly(A) RNAs by enhanced interactome capture. Eluates obtained by previous method (oligo(dT)) or enhanced interactome capture (LNA2.T) were reverse transcribed using the SuperScript™ II Reverse Transcriptase kit (Thermo) and the abundance of the indicated mRNAs was determined by QPCR in a QuantStudio™ 7 Flex Real-Time PCR System (Thermo). Primers were design to prevent amplification of genomic DNA. The sequences of the employed primers are.
Figure 5:
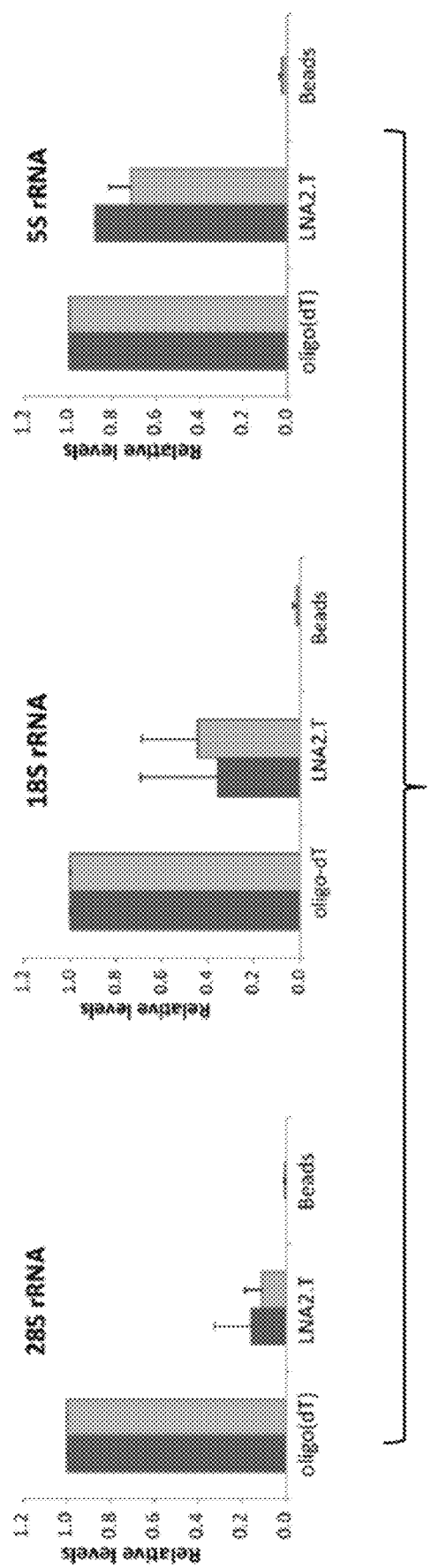

FIG. 5 shows depletion of specific rRNAs by enhanced interactome capture. Eluates obtained by previous method (oligo(dT)) or enhanced interactome capture (LNA2.T) were reverse transcribed using the SuperScript™ II Reverse Transcriptase kit (Thermo) and analyzed by QPCR in a QuantStudio™ 7 Flex Real-Time PCR System (Thermo). The sequences of the used primers are:

```
                                    (SEQ ID NO: 5)
28S Fw      TTA CCC TAC TGA TGA TGT GTT GTT G.

(SEQ ID NO: 6)
28S Rv      CCT GCG GTT CCT CTC GTA.

(SEQ ID NO: 7)
18S Fw      GAAACTGCGAATGGCTCATTAAA.

(SEQ ID NO: 8)
18S Rv      CACAGTTATCCAAGTGGGAGAGG;

(SEQ ID NO: 9)
5S Fw       GGC CAT ACC ACC CTG AAC GC;
and (SEQ ID NO: 10)
5S Rv       CAG CAC CCG GTA TTC CCA GC.
```

Figure 6:
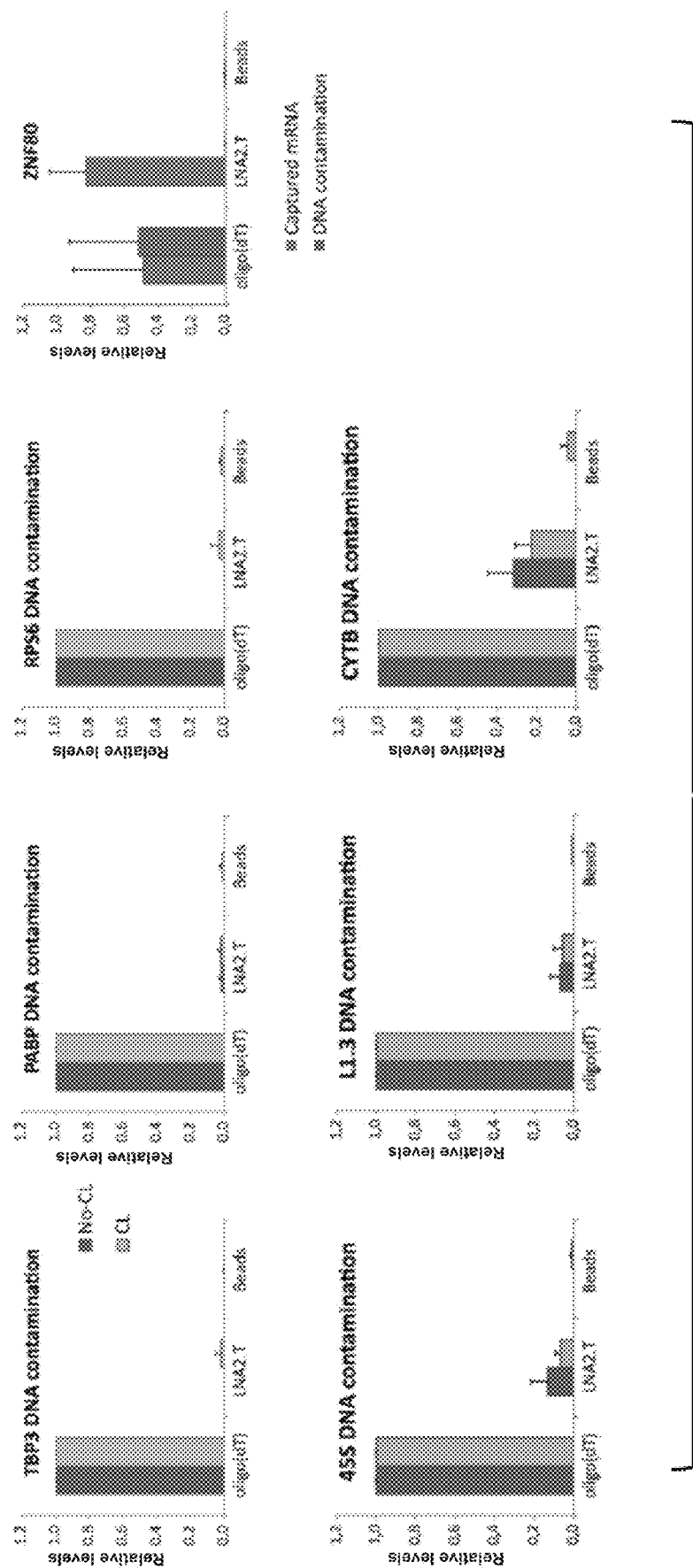

FIG. 6 shows that enhanced interactome capture leads to a profound reduction of the DNA-contamination. Eluates obtained by previous method (oligo(dT)) or enhanced interactome capture (LNA2.T) were analyzed by QPCR in a QuantStudio™ 7 Flex Real-Time PCR System (Thermo) without being subjected to reverse transcription. A wide range of gene classes was analyzed including genes with numerous copies in the genome that are common contaminants. Analyzed genes comprise the nuclear protein-coding genes TBP3, PABP, RPS6 and ZNF80, the 45S rDNA, the retrotansposon L1.3 and the mitochondrial protein-coding gene CYTB. Levels of ZNF80 gen and mRNA were determined using identical primers. ZNF80 mRNA levels were determined after DNA digestion with TURBO Dnase (Thermo) and reverse transcription using the SuperScript™ II Reverse Transcriptase kit (Thermo). The sequences of the used primers are:

```
                                    (SEQ ID NO: 11)
    45S Fw:        TCGCTGCGATCTATTGAAAG;

(SEQ ID NO: 12)
    45S Rv:        AGGAAGACGAACGGAAGGAC;
```

```
                           (SEQ ID NO: 13)
L1.3 Fw:        TGAAAACCGGCACAAGACAG;

(SEQ ID NO: 14)
L1.3 Rv:        CTGGCCAGAACTTCCAACAC;

(SEQ ID NO: 15)
CYTB Fw:        ACCCCCTAGGAATCACCTCC;

(SEQ ID NO: 16)
CYTB Rv:        GCCTAGGAGGTCTGGTGAGA;

(SEQ ID NO: 17)
ZNF80_Fw:       CTGTGACCTGCAGCTCATCCT;

(SEQ ID NO: 18)
ZNF80_Rv:       TAAGTTCTCTGACGTTGACTGATGTG;

(SEQ ID NO: 19)
TBP3 Fw:        GTGAGAAGATGGATGTTGAGTTG;

(SEQ ID NO: 20)
TBP3 Rv:        GATAGCAGCACGGTATGAGC;

(SEQ ID NO: 21)
RPS6 Fw:        TGAAGTGGACGATGAACGCA;

(SEQ ID NO: 22)
RPS6 Rv:        CCATTCTTCACCCAGAGCGT;

(SEQ ID NO: 23)
PABPC1 Fw:      CCAGGCTCACCTCACTAACC;
and (SEQ ID NO: 24)
PABPC1 Rv:      CTGGCTGGTAGGGGTTGATT;
```

FIG. 7 shows an efficient capture of RNA-binding proteins by enhanced interactome capture. Proteins captured by previous method (oligo(dT)) or enhanced interactome capture (LNA2.T) were separated by SDS-PAGE and silver-stained (A) or subjected to western blot against specific bona fide RBPs (B). (A) A distinct band pattern in +UV samples indicates differential protein capture by the two protocols. Black and blue arrows indicate examples of specific bands that are depleted or enriched in LNA2.T in comparison to oligo(dT). (B) Western blot indicates greater capture of the RBPs UnR, Nono and HuR by enhanced interactome capture.

Figures 8A, 8B:
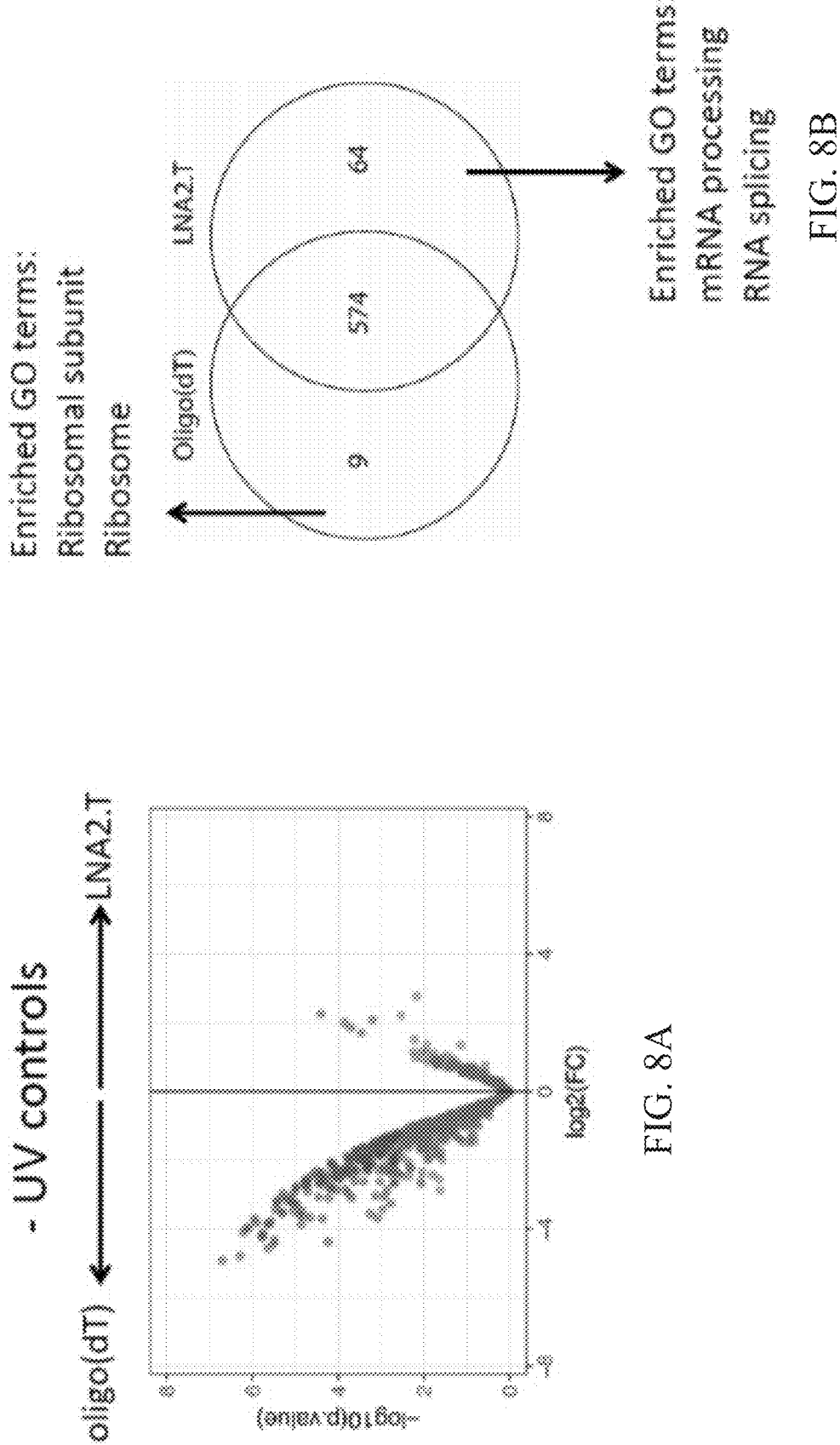

FIG. 8 shows reduced protein contamination and increase RBP detection by enhanced interactome capture. Proteins captured by the previous method (oligo(dT)) or enhanced interactome capture (LNA2.T) were vacuum concentrated in a SpeedVac concentrator system (Thermo), processed by SP3, fractionated and analyzed by quantitative proteomics. (A) Volcano plot showing the distribution of detected protein in non-irradiated controls. There is a substantial reduction on the number and amount of contaminant proteins when LNA2.T is applied. (B) Venn diagram of captured proteins with oligo(dT) and LNA2.T. LNA2.T identifies a larger number of proteins (638 vs 583). Gen Ontology (GO) analyzes indicate that many of them are known mRNA interactors. In addition, LNA2.T lacks 9 proteins that are mostly connected with rRNA and not mRNA metabolism, suggesting reduced protein contamination by LNA2.T. Examples of these proteins as well as of bona-fide RBPs that are enriched in LNA2.T are presented in FIG. 8C.

FIG. 9 shows that eRIC captures polyadenylated RNA and covalently crosslinked proteins with high specificity. (A) Schematic representation of the eRIC procedure. RBPs are crosslinked to RNAs in vivo by irradiating cells with 254 nm UV light. Crosslinked proteins are isolated employing a LNA-modified probe, stringently washed under high temperature and low salt conditions, eluted with RNase, and identified by MS. A comparison with the previous RIC protocol is depicted in the right panel. (B and C) Nucleic acids isolated by eRIC, RIC or using uncoupled beads along the eRIC protocol ("Beads") were analyzed using a 6000 Pico bioanalyzer (B) or by RT-qPCR (C). Note that the pre-elution step ("Pre-elu") incorporated in eRIC leads to an effective pre-elution of rRNAs, specially the 28S rRNA, without compromising capture of poly(A) RNAs. Data are shown as mean+s.d. from at least three biologically independent experiments. (D and E) Isolated proteins were separated by SDS-PAGE and silver-stained (D), or analyzed by western blot with antibodies to the positive control RBPs UNR, NonO and HuR (E). Re-elu: heat elution performed after RNAse treatment. Note that a minor fraction of HuR appears to be associated with non-polyadenylated RNAs[38].

FIG. 10 shows superior performance of eRIC in RBP detection. (A) Scheme of the workflow of the comparative analysis of eRIC and RIC. (B) Volcano plots displaying the log2-fold change (FC) in crosslinked over non-crosslinked samples (x-axis) and the P values (y-axis) of the proteins identified by eRIC (right) and RIC (left). Proteins with p-values<0.05 and FC≥2 were considered significantly enriched and are depicted in red. (C) Density of log2-FC between irradiated and non-irradiated samples of proteins identified by eRIC (red) and RIC (blue). (D) Scatter plot comparing the averaged log2-FC in irradiated over non-irradiated samples of proteins detected by eRIC (y-axis) and RIC (x-axis). Hits recovered by both eRIC and RIC are displayed in green, hits unique to eRIC or RIC in magenta and blue, respectively, and proteins identified as background by both methods are shown in black. (E) Venn diagram comparing the number of hits identified by eRIC and RIC. (F) Normalized signal sum in irradiated and non-irradiated samples of the 97 hits exclusively identified by eRIC. *** indicates p<0.001 (Wilcoxon signed-rank test). (G) Number of known RBPs, enzymes, enigmRBPs[4] and metabolic enzymes identified by eRIC and RIC. (H) UpSet plot showing the intersections between the eRIC and RIC experiments presented here and previously published RBP datasets. Data shown in b-h correspond to two biologically independent experiments.

FIG. 11 shows a differential RBP enrichment with eRIC. (A) Unsupervised clustering and GO analysis of proteins whose enrichments in irradiated over non-irradiated samples differ significantly (p-value<0.05 and FC>2, 144 proteins) between eRIC and RIC. Three main clusters are observed that comprise RBPs preferentially recovered by RIC (top) or eRIC (middle and bottom). Biological process GO terms enriched for each cluster are shown. Upper: "ribosome biogenesis" ((−log10 (p−value)=39.95; enrichment=40.6), middle: "mRNA processing" (18.36; 14.85), bottom: "mRNA splicing via spliceosome" (33.48; 52.4), "mRNA transport" (8.52; 30.85) and "regulation of mRNA stability" (4.04; 17.08). (B) Fold change in irradiated over non-irradiated samples of representative example RBPs captured by eRIC and RIC. Data are shown as mean and standard deviation from two biologically independent experiments.

FIG. 12 shows superior performance of eRIC in comparative analyses of RBP responses. (A) Experimental design: Jurkat cells were incubated for 6 h with 0.5 mM DMOG or the vehicle DMSO. After irradiation, cells were lysed and lysates equally split for eRIC or RIC analyses. n=2 independent experiments. (B) Pie charts summarizing the response of the RNA-bound proteomes to DMOG treatment identified by eRIC (right) or RIC (left). The number and percentage of proteins displaying constant (grey), increased (green) or decreased (violet) RNA association upon DMOG is shown. (C) Venn diagram comparing the number of DMOG-responsive RBPs identified by each method. (D) Volcano plots displaying the p-values (y-axis) and the log2-fold change (FC) in DMOG- vs vehicle-treated and irradiated samples (x-axis) of the proteins detected by eRIC (right) and RIC (left). Proteins with p-values<0.05 and consistent FC of at least 10% in each replicate were considered as hits and are depicted in red. (E) Density of log2-FC in DMOG- over vehicle-treated samples of the proteins identified by eRIC (red) and RIC (blue). (F) Scatter plots of detected proteins comparing the log2 ratios (DMOG/vehicle) of two independent experiments. (G) Heat map showing the protein log2 ratios (DMOG/vehicle) of eRIC/RIC hits. Hits were divided according to their occurrence in eRIC and/or RIC and clustered. (H) Representative biological processes and cellular components enriched among the DMOG-responsive RBPs identified by eRIC and/or RIC. (I) Examples of protein complexes or functionally related proteins that respond to DMOG with statistical significance.

FIG. 13 shows that eRIC identifies m6A-responsive RBPs in vivo. (A) m6A dot blot of Jurkat cells treated with 0.5 mM DMOG or vehicle for 6 h, using two independent antibodies (Antibody 1: Abcam, Antibody 2: SySy). (B) Overlap between DMOG-responsive RBPs identified by eRIC/RIC and m6A-regulated RBPs previously reported by Edupuganti et al.[21] or Arguello et al.[20]. Between brackets are the number of proteins with directions of DMOG-induced changes that coincide with previous reports. (C) Normalized signal sum in eRIC and RIC samples of representative examples of reported m6A-readers (left), m6A-repelled RBPs (middle), and RBPs insensitive to m6A (right). eRIC and RIC values are expressed relative to the respective untreated control (-UV, DMSO). Data are shown as mean and standard deviation from two biologically independent experiments. * indicates FDR<0.05.

SEQ ID NOs: 1 to 25 show sequences of oligonucleotides as used in the context of the invention.

EXAMPLES

Introduction

The inventive enhanced RNA interactome capture (eRIC) allows the comprehensive and unbiased identification of poly(A) RNA-associated proteins in vivo. The method relies on the utilization of oligo(T) probes in which some of the bases are substituted with locked nucleic acids (LNA), a type of nucleotide analogue in which the conformation of the sugar ring is locked by a methylene bridge.

In detail, one embodiment of the inventive method comprises the series of steps, as follows: UV light (typically of 254 nm or 365 nm) is applied to cultured cells, tissues or organisms to covalently crosslink RNA-binding proteins (RBPs) to RNA in vivo.

Subsequently, the material is lysed under denaturing conditions that include 500 mM lithium chloride and 0.5% lithium dodecyl sulphate (see lysis buffer composition below).

To shear genomic DNA and to reduce viscosity, samples are passed 3-5 and 5-10 times through syringes with 22G (gauge 0.7 mm diameter) and 27G needles (gauge 0.4 mm diameter), respectively. Lysates are incubated at 60° C. for 10-15min and cleared by centrifugation (230-500×g for 3-5 min at 4° C.). poly(A) RNA-protein complexes are captured by incubation of the cleared extract at 37-40° C. for 30-60 min with LNA-bearing oligo(T) coupled to a solid support such as magnetic beads.

Then, captured complexes are washed at 37-40° C., once with lysis buffer and twice with each of the buffers 1, 2 and 3 (see composition below). Beads are magnetized and subjected to a stringent pre-elution in pure water at 40° C. for 5-10min.

The RBPs bound to poly(A) RNA are released by RNA digestion with RNases A and T1 at 37° C., and then concentrated by SpeedVac to minimize sample losses. Finally, protein samples are prepared by Single-Pot Solid-Phase-enhanced Sample Preparation (SP3) and subjected to quantitative mass spectrometry.

Materials and Methods

Cell Culture. Jurkat cells (DSMZ, ACC-282) were maintained as a suspension culture in 175 $cm^2$ flasks (Falcon, 353028) in RPMI 1640 medium (Thermo Fisher Scientific, 21875034) supplemented with 10% heat inactivated Fetal Bovine Serum (Gold, GE Healthcare) and penicillin/streptomycin (Sigma-Aldrich, P4333) in a humidified incubator at 37° C. and 5% $CO_2$.

Coupling of the LNA-Modified Oligonucleotide to Carboxylated Magnetic Beads. The capture probe (HPLC purified; Exiqon) is composed of a primary amine at the 5'end, a flexible C6 linker, and 20 thymidine nucleotides in which every other nucleotide is a LNA: /5AmMC6/+TT+TT+TT+TT+TT+TT+TT+TT+TT+TT (+T: LNA thymidine, T: DNA thymidine)[10]. The probe was resuspended in nuclease-free water (Ambion) to a final concentration of 100 mM and coupled in DNA low binding tubes (Eppendorf) to carboxylated magnetic beads (Perkin Elmer, M-PVA C11) through the 5' amine as follows or kept at −20° C. until coupling. 50 mg/mL of bead slurry were washed 3 times with 5 volumes of 50mM 2-(N-morpholino)ethanesulfonic acid (MES) buffer pH 6. A 20 mg/mL solution of N-(3-dimethylaminopropyl)-N'-ethylcarbodiimide hydrochloride (EDC-HC1; Sigma-Aldrich) in MES buffer was freshly prepared. 5 volumes were combined with 1 volume of 100 mM probe solution and this added to pelleted washed beads coming from 1 volume of bead slurry (for one capture: 1.5mL EDC solution +300 mL probe solution +300 mL bead slurry). Coupling was performed for 5 h at 50 ° C. and 800 rpm, with occasional pelleting. Beads were then washed twice with PBS and then incubated with 200 mM ethanolamine pH 8.5 for 1 h at 37 ° C. 800 rpm to inactivate any residual carboxyl residue. Coupled beads were finally washed three times with 1 M NaCl, and stored in 0.1% PBS-Tween at 4° C.

Recycling of LNA2.T-Coated Beads. Coupled beads can be reused several times. To do so, the poly(A) stretches interacting with the LNA probe, expected to be resistant to the RNA digestion, have to be eluted by other mean. Also, any trace of RNases from the elution has to be eliminated. Beads were reused a few times in this work and at least 8 times in other works, with optimal results.

Coupled beads employed for a capture (300 mL) were resuspended in 400 mL of nuclease-free water (Ambion), transferred to a 1.5 mL tube and incubated for 5-10 min at 95 ° C. 800 rpm. Immediately afterwards, before bead slurry cool down, beads were collected by magnetic force, and the supernatant discarded. Beads were then washed 3 times with 5 volumes of water and 3 times with 5 volumes of lysis buffer and stored in 0.1% PBS-Tween at 4° C. until use.

RBP Isolation Using eRIC. Cell lysis. 1.0-1.3×$10^8$ proliferating Jurkat cells at a density of about 1-1.5×$10^6$ cells/mL were employed per sample. Where stated, 0.5mM DMOG (Cayman Chemical Company, 71210) or an equivalent volume of Dimethyl Sulfoxide (DMSO) (vehicle, Merck 1.02950.0500) was added to the culture medium for 6 h prior to processing. The DMSO concentration in the medium was 0.023% v/v. Cells were collected by centrifugation at 400g for 5 min at 4° C., resuspended in 40 mL of cold PBS and split into two 145×20 mm petri dishes (Greiner Bio-One, 639102), which were deposited on a metal plate pre-cooled on ice and irradiated with 150 mJ/cm$^2$ at 254 nm UV light in a Spectrolinker XL-1500 (Spectronics Corporation). Irradiation was omitted in –UV controls. While constantly maintaining 4° C., cells were transferred to 50 mL conical centrifuge tubes, pelleted at 400 g for 5 min, and lysed in 7.5-10 mL of ice-cold lysis buffer (see composition below) supplemented with Complete Protease Inhibitor Cocktail (Roche, 11873580001). To enhance homogenization, samples were passed 3-5 and 6-10 times through syringes with 22 Gauge (0.7 mm diameter) and 27 Gauge needles (0.4 mm diameter), respectively, snap frozen in liquid nitrogen, and kept at –80 °C. for several days until further processing.

Capture of RNP complexes. Cell lysates were thawed in a 37° C. water bath, incubated for 15 min at 60° C., quickly cooled down on ice and clarified 5 min at max speed and 4° C. 5 mM DTT extra was added to the samples. LNA2.T-coupled beads were equilibrated in lysis buffer (3 buffer exchanges with 3 volumes of lysis buffer each). After saving 100 mL as input, lysates were incubated with 300 mL of equilibrated LNA2.T coupled beads for 1 h at 37-40° C. (inside an incubator) with gentle rotation to capture RNA-protein complexes. Beads were collected with a magnet, and supernatant transferred to a fresh tube for a second round of capture. Beads were subjected to successive rounds of washes, each of them performed for 5 min with gentle rotation at 37-40° C. (inside an incubator) with 10 mL of the corresponding buffer pre-warmed to 37-40° C. The inventors performed one wash with lysis buffer and two successive washes with each of the buffers 1, 2 and 3 (see composition below). Pre-elution was performed in 220 mL of nuclease-free water (Ambion) for 5 min at 40° C. and 800 rpm. Afterwards, the bead suspension was divided into two aliquots, one of 200 mL for the RNase-mediated elution for protein analysis and one of 20 mL that was heat-eluted for RNA/DNA analyses. For the RNase-mediated elution, beads were resuspended in 150 mL of 1× RNase buffer (see composition below), 5mM DTT, 0.01% NP40, ~200U RNase Ti (Sigma-Aldrich, R1003-100KU) and ~200U RNase A (Sigma-Aldrich, R5503) and incubated at 37° C. 800 rpm for 30-60 min. Beads were then collected with a magnet, and the supernatant transferred to a fresh tube, which was placed again on a magnet (to fully remove any trace of beads) before saving the supernatant. Eluates were maintained on ice until finishing the second round of capture. Then, combined eluates were supplemented with 2 mL 10% SDS and concentrated using a SpeedVac until reaching a volume of less than 100 mL (30-45 min at 37° C.), snap frozen and stored at –80 °C. Heat elution was performed on the beads reserved ad hoc with 15 mL of elution buffer (see composition below) at 95° C. 800 rpm for 5 min. Beads were immediately collected, and supernatant quickly recovered (before temperature drops). Any trace of beads was eliminated by a second round of collection as explained before.

Buffers

Lysis buffer: 20 mM Tris-HCl (pH 7.5), 500 mM LiCl, 1 mM EDTA, 5 mM DTT, 0.5% (w/v) LiDS.

Buffer 1: 20 mM Tris-HCl (pH 7.5), 500 mM LiCl, 1 mM EDTA, 5 mM DTT, 0.1% (w/v) LiDS.

Buffer 2: 20 mM Tris-HCl (pH 7.5), 500 mM LiCl, 1 mM EDTA, 5 mM DTT, 0.02% (v/v) NP40.

Buffer 3: 20 mM Tris-HCl (pH 7.5), 200 mM LiCl, 1 mM EDTA, 5 mM DTT, 0.02% (v/v) NP40.

Elution buffer: 20 mM Tris-HCl (pH 7.5), 1 mM EDTA.

10× RNase buffer: 100mM Tris-HCl (ph 7.5), 1.5mM NaCl.

RBP Isolation Using RNA Interactome Capture (RIC). Cell lysis was performed as for eRIC, and RBP isolation was achieved as described before[2,31]. Briefly, lysates were thawed in a 37° C. water bath and after taken 100 µL as input they were incubated with 300 µL of equilibrated oligo(dT)$_{25}$ magnetic beads (NEB) at 4° C. for 1 h with gentle rotation. Beads were washed with 10 mL of ice-cold buffers. RNP complexes were eluted in 165 µL of elution buffer for 5 min at 55° C. and 800 rpm. An aliquot of 15 µL was taken and used for RNA/DNA analyses. The remaining 150 µL were combined with 10× RNase buffer, 1M DTT and 1% NP40 (final concentrations: 1× RNase buffer, 5 mM DTT, 0.01% NP40) and ~200U RNase T1 and RNase A (Sigma-Aldrich). RNA was digested for 60 min at 37° C. Two rounds of capture were performed and combined eluates were concentrated and stored as described for eRIC. Final volume of RIC eluates was adjusted to the volumes of the corresponding eRIC eluates.

Sample Preparation for Mass Spectrometry and TMT Labeling. Captured proteins were reduced in 10 mM dithiothreitol in 50 mM HEPES pH 8.5 at 56 °C. for 30 min, and alkylated with 20 mM 2-chloroacetamide in 50 mM HEPES pH 8.5 for 30 min at RT in the dark. Samples were prepared using the SP3 protocol[11]. Proteins were digested by trypsin (Promega) at 37° C. ON using an enzyme to protein ratio of 1:50. Peptides were labeled with TMT10plex Isobaric Label Reagent (Thermo Fisher Scientific) according to the manufacturer's instructions. For further sample clean up an OASIS HLB µElution Plate (Waters) was used. Offline high pH reverse phase fractionation was carried out on an Agilent 1200 Infinity high-performance liquid chromatography system, equipped with a Gemini C18 column (3 µm, 110 Å, 100×1.0 mm, Phenomenex).

Mass Spectrometry Data Acquisition. An UltiMate 3000 RSLC nano LC system (Dionex) fitted with a trapping cartridge (µ-Precolumn C18 PepMap 100, 5 µm, 300 µm i.d.×5 mm, 100 Å) and an analytical column (nanoEase™ M/Z HSS T3 column 75 µm×250 mm C18, 1.8 µm, 100 Å, Waters) were employed. Trapping was carried out with a constant flow of solvent A (0.1% formic acid in water) at 30 µL/min onto the trapping column for 6 minutes. Subsequently, peptides were eluted via the analytical column with a constant flow of 0.3 µL/min with increasing percentage of solvent B (0.1% formic acid in acetonitrile) from 2% to 4% in 4 min, from 4% to 8% in 2 min, from 8% to 28% in 96 min, and finally from 28% to 40% in 10 min. The outlet of the analytical column was coupled directly to a QExactive plus mass spectrometer (Thermo Fisher Scientific) using the proxeon nanoflow source in positive ion mode.

The peptides were introduced into the QExactive plus via a Pico-Tip Emitter 360 µm OD×20 gm ID; 10 µm tip (New Objective) applying a spray voltage of 2.3 kV. The capillary temperature was set at 320° C. Full mass scan was acquired with mass range 350-1400 m/z in profile mode in the FT with resolution of 70000. The filling time was set at maximum of 100 ms with a limitation of 3×10⁶ ions. Data dependent acquisition was performed with the resolution of the Orbitrap set to 35000, with a fill time of 120 ms and a limitation of 2×10⁵ ions. A normalized collision energy of 32 was applied. The instrument was set to alternate between MS and data-dependent MS/MS based acquisition with up to a maximum of 10 MS/MS events per cycle. A minimum AGC trigger of 2e2 and a dynamic exclusion time of 30 s were used. The peptide match algorithm was set to 'preferred' and charge exclusion to 'unassigned', charge states +1 and +5 to +8 were excluded. MS/MS data was acquired in profile mode.

Mass spectrometry data analysis. IsobarQuant[32] and Mascot (v2.2.07) were used to process the acquired data, which was searched against the Uniprot Homo sapiens proteome database UP000005640, which contains common contaminants and reversed sequences. The following modifications were included into the search parameters: Carbamidomethyl (C) and TMT10 (K) (fixed modifications), Acetyl (N-term), Oxidation (M) and TMT10 (N-term) (variable modifications). A mass error tolerance of 10 ppm and 0.02 Da was set for the full scan (MS1) and the MS/MS spectra, respectively. A maximum of two missed cleavages were allowed and the minimal peptide length was set to seven amino acids. At least two unique peptides were required for protein identification. The false discovery rate on peptide and protein level was set to 0.01. The R programming language (ISBN 3-900051-07-0) was used to analyze the raw output data of IsobarQuant. Potential batch effects were removed using the limma package[33]. A variance stabilization normalization was applied to the raw data using the vsn package[34]. Individual normalization coefficients were estimated for crosslinked and non-crosslinked conditions. During the DMOG versus DMSO comparison, an additional blocking factor for the protocol (RIC or eRIC) was chosen. Normalized data were tested for differential expression using the limma package. The replicate factor was included into the linear model. For comparisons between crosslinked vs non-crosslinked, hits were defined as those proteins with a false discovery rate of less than 5% and a fold change greater than 2. In eRIC/RIC comparative experiments, proteins were first tested for their enrichment over −UV controls, and the intensity of the proteins enriched in at least one condition were compared in the corresponding +UV samples. The R package fdrtool[35] was employed to calculate false discovery rates using the t values from the limma output. Proteins with a false discovery rate smaller 5% and a consistent fold change of at least 10% in each replicate were defined as hits. The ggplot2 R package ([36]) was used to generate the graphical representations.

Hit classification and GO analysis. RBPs identified in the "single point" eRIC/RIC experiments were categorized as previously described based on the curated set of human RIC studies[5] and a curated set of RBPs[12]. Overlaps with other RIC data sets were displayed in UpSet plots[37].

Comparison of DMOG-responsive hits identified by eRIC and RIC with previously reported m6A-regulated RBPs[20,21] was conducted using Venny 2.1.0 (Oliveros, J. C. (2007-2015), http://bioinfogp.cnb.csic.es/tools/venny/index.html). Analysis was restricted to those proteins detected by the eRIC/RIC comparative experiments. Fisher's exact tests were used to calculate enrichment of m6A-responding proteins among eRIC and RIC samples.

GO-term enrichment analysis were performed with AmiGO 2 (powered by PANTHER), using the following parameters: analysis type: PANTHER overrepresentation test; reference list: Homo sapiens (all genes in database); annotation data set: GO biological process complete or GO cellular component complete, as indicated; test type: Fisher's exact with FDR multiple test correction. Overrepresented GO terms were manually curated, and only selected terms were included in the main figures due to space constrains. The ggplot2 R package ([36]) was used to generate the graphical representations.

Bioanalyzer and real time-PCR. The concentration of captured RNA (heat-eluted) was estimated using a NanoDrop spectrophotometer (Thermo Fisher Scientific). To determine the profile of captured RNA, 1μL of each sample was diluted to 5-10 ng/μL and analyzed in an Agilent 2100 Bioanalyzer System using the RNA 6000 Pico Kit, following the manufacturer's indications. Where stated, total RNA from whole-cell lysates was purified using the Quick-RNA MicroPrep kit (Zymo) and analyzed similarly. 2-5 μL of the undiluted captured RNA were reverse transcribed into cDNA using SuperScript II (Life Technologies) and random hexamers (Life Technologies), according to the manufacturer's instructions. Real time quantitative PCR was performed using SYBR Green PCR Master Mix (Life Technologies, 4309155) in a QuantStudio 6 Flex system (Life Technologies) with the following primers (all from 5' to 3', forward: f, reverse: r):

```
28S rRNA
(f: TTACCCTACTGATGATGTGTTGTTG (SEQ ID No. 5), r: CCTGCGGTTCCTCTCGTA (SEQ ID No. 6)),

RPS6
(f: TGAAGTGGACGATGAACGCA (SEQ ID NO. 21), r: CCATTCTTCACCCAGAGCGT (SEQ D No. 22)),

ZNF80
(f: CTGTGACCTGCAGCTCATCCT (SEQ ID No. 17), r: TAAGTTCTCTGACGTTGACTGATGTG (SEQ ID NO.18)).

From ²: β-actin
(r: CGCGAGAAGATGACCCAGAT (SEQ ID No. 4), f: TCACCGGAGTCCATCACGAT (SEQ ID No. 3)), GAPDH
(f: GTGGAGATTGTTGCCATCAACGA (SEQ ID No. 25), r: CCCATTCTCGGCCTTGACTGT (SEQ ID No. 2))
and 18S rRNA
(f: GAAACTGCGAATGGCTCATTAAA (SEQ ID No. 7), r: CACAGTTATCCAAGTGGGAGAGG (SEQ ID No. 8)).

From ³: L1.3
(f: TGAAAACCGGCACAAGACAG (SEQ ID No. 13), r: CTGGCCAGAACTTCCAACAC (SEQ ID No. 14)).
```

Western blotting and silver staining. eRIC/RIC quality control. Proteins co-purified by eRIC or RIC or present in whole cell lysates (inputs) were separated by SDS-PAGE and subjected to silver staining following standard procedures, or transferred onto a nitrocellulose membrane and analyzed by western blotting. Primary antibodies against the following proteins were used: Cold shock domain-containing protein E1 (CSDE1)/UNR (Proteintech, 13319-1-AP), Non-POU domain-containing octamer-binding protein (NonO) (Novus Biologicals, NBP1-95977), ELAV-like protein 1 (ELAVL1)/Hu-antigen R (HuR) (Proteintech, 11910-

1-AP). As a secondary antibody a Goat anti-rabbit IgG HRP (Santa Cruz Biotechnology) was employed.

Analysis of DMOG effects. Proliferating Jurkat cells at a density of about $1 \times 10^6$ cells/mL were incubated with 0.5 mM DMOG (Cayman Chemical Company, 71210) or an equivalent volume of Dimethyl Sulfoxide (DMSO) (vehicle, Merck 1.02950.0500) for 6 h. Subsequently, cells were pelleted (400g 5 min 4° C.), washed with ice-cold PBS, and lysed in ice-cold RIPA buffer (50mM Tris-HCl, pH 7.4, 1% NP-40, 0.5% Na-deoxycholate, 0.1% SDS, 150 mM NaCl, 2 mM EDTA, 50 mM NaF) supplemented with proteinase inhibitors (Roche, 11873580001) and phosphatase inhibitors (Sigma-Aldrich, 04906845001). After clarification, proteins were separated by SDS-PAGE and transferred onto a nitrocellulose membrane. Primary antibodies to the following proteins were used: anti-GAPDH (Sigma-Aldrich, G9545), all the rest from Cell Signaling: phospho-4EBP1 (Ser65) (9451S), 4EBP1 (9644S), phospho-p70 S6 Kinase (Thr389) (9205), p70 S6 Kinase (2708), phospho-ULK1 (Ser757) (14202), ULK1 (8054), phospho-mTOR(Ser2448) (5536P), mTOR (2983). A Goat anti-rabbit IgG HRP (Santa Cruz Biotechnology) was used as secondary antibody.

m6A dot blotting. Aliquots of the heat-eluted RNA of the same eRIC samples analyzed by MS (-UV controls) were used to estimate m6A levels. RNA was incubated for 10 min at 65° C. and immediately placed on ice. Concentration was estimated with a NanoDrop spectrophotometer (Thermo Fisher Scientific) and serial dilutions were prepared in order to obtain 100, 50, 25 and 12.5 ng/µL. 1µL of each dilution was directly pipetted onto a Zeta Probe membrane (Bio-Rad), air dried for ~10 min, and crosslinked twice with 120 mJ/cm$^2$ at 254 nm in a Spectrolinker XL-1500 (Spectronics Corporation). The membrane was washed with 0.05% PBS-Tween (PBS-T), and blocked for 1 h with 5% skimmed milk in PBS-T. Primary antibodies were incubated in blocking solution overnight at 4° C., followed by three rinses with PBS-T, secondary antibody incubation in blocking solution for 1 h at RT, three washes with PBS-T and development using ECL (Millipore, WBKLS0500). Antibodies used were: anti-m6A (Abcam, ab151230, 1:2000 and Synaptic Systems, 202 003, 1:2000) and Goat anti-Rabbit IgG-HRP (Abcam, 1:20000).

Poly(A) Tail-Mediated Capture of RBPs: Considerations

With suitable tools for de novo RBP discovery now in hand, the inventors wanted to build on the principle of RIC and develop a method that is highly performant in comparative studies. To reach this goal, the inventors aimed to reduce DNA and rRNA contaminations which could contribute inadvertently co-purifying proteins and increase background RBPs.

Figure 9A:
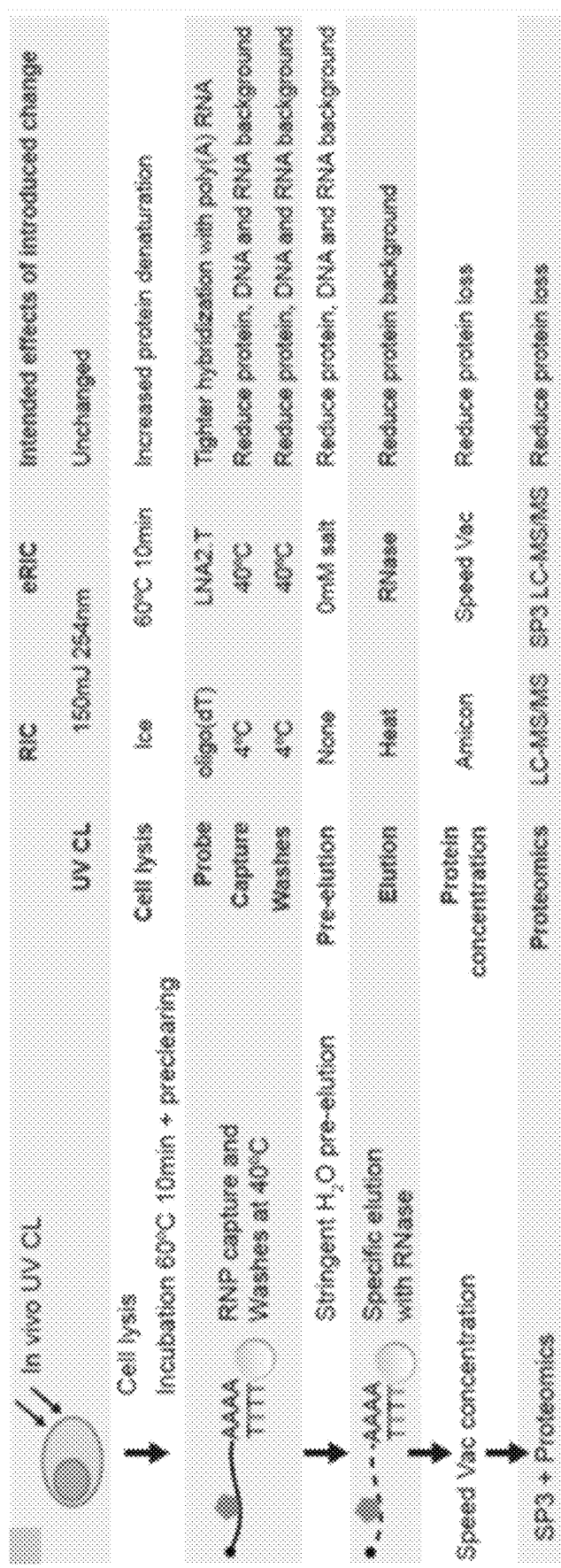

To minimize protein-protein interactions that resist the denaturing capture conditions, the inventors pre-incubated cell lysates at 60° C. for 10-15min[7], followed by centrifugation to remove insoluble material (FIG. 9a). By using a modified probe with locked nucleic acids (LNA), which positions oligonucleotides optimally for hybridization with RNA, the inventors profoundly increased the melting temperature between the capture probe and poly(A) tails (from ~40° C. to ~77° C.), permitting more stringent purification conditions. A 20-mer bearing an LNA-T at every other position (LNA2.T) had previously been shown to effectively capture mRNA[10]. The probe design also includes a flexible C6 linker and a primary amino group at the 5' end, used to couple the LNA oligo to carboxylated magnetic beads (see methods for detailed procedure). With this probe, all steps of the protocol, including capture and all washes, could be executed at 37-40° C. instead of 4° C. (FIG. 9a). Since salt stabilizes RNA-RNA and RNA-DNA duplexes, and hence favors contaminating nucleic acid pull down, the inventors exploited the stability of LNA2.T-poly(A) RNA duplexes and incorporated a pre-elution step with pure water at 40° C. (FIG. 9a). This step proved instrumental for the efficient elimination of contaminant nucleic acids, such as rRNA and genomic DNA, without interfering with poly(A) capture (see below).

In RIC, the RNA pull down and the washes are performed at 4° C. to avoid interference with the oligo(dT)/poly(A) hybridization. This is followed by temperature-mediated elution at 50-55° C. (FIG. 9a). The increase in elution temperature could cause the co-elution of contaminants, including proteins directly associated with the beads employed for the pull down. To improve the specificity of the elution and to decrease background contaminants, the inventors substituted the heat elution by RNase treatment at 37° C. (FIG. 9a). This elution strategy is more specific for RNA-bound proteins and is executed at a lower temperature than the washes. The inventors termed this approach, which involves the use of the LNA2.T probe, increased capture and wash temperatures, the pre-elution and the specific RNase-based elution, 'enhanced RNA-Interactome Capture (eRIC)'. The inventors directly compared the performance of RIC and eRIC using Jurkat cells, a cell type characterized by a large nuclear compared to a relatively modest cytoplasmic volume. All experiments were performed in parallel.

Figure 9B:
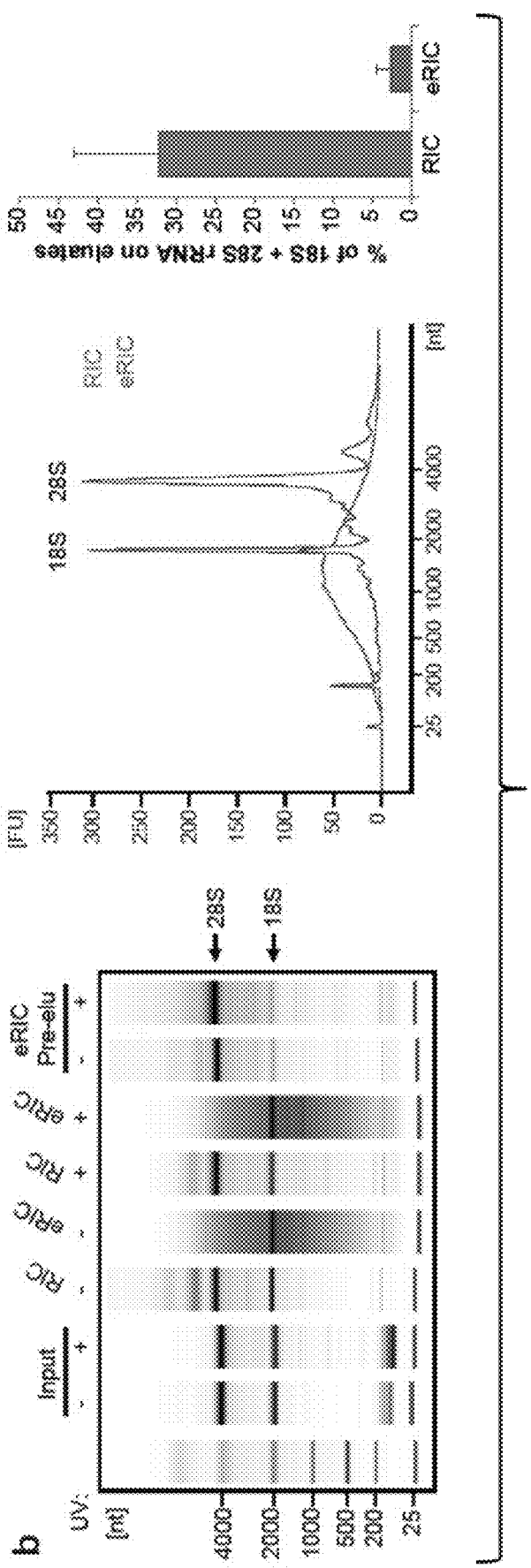
Figure 9C:
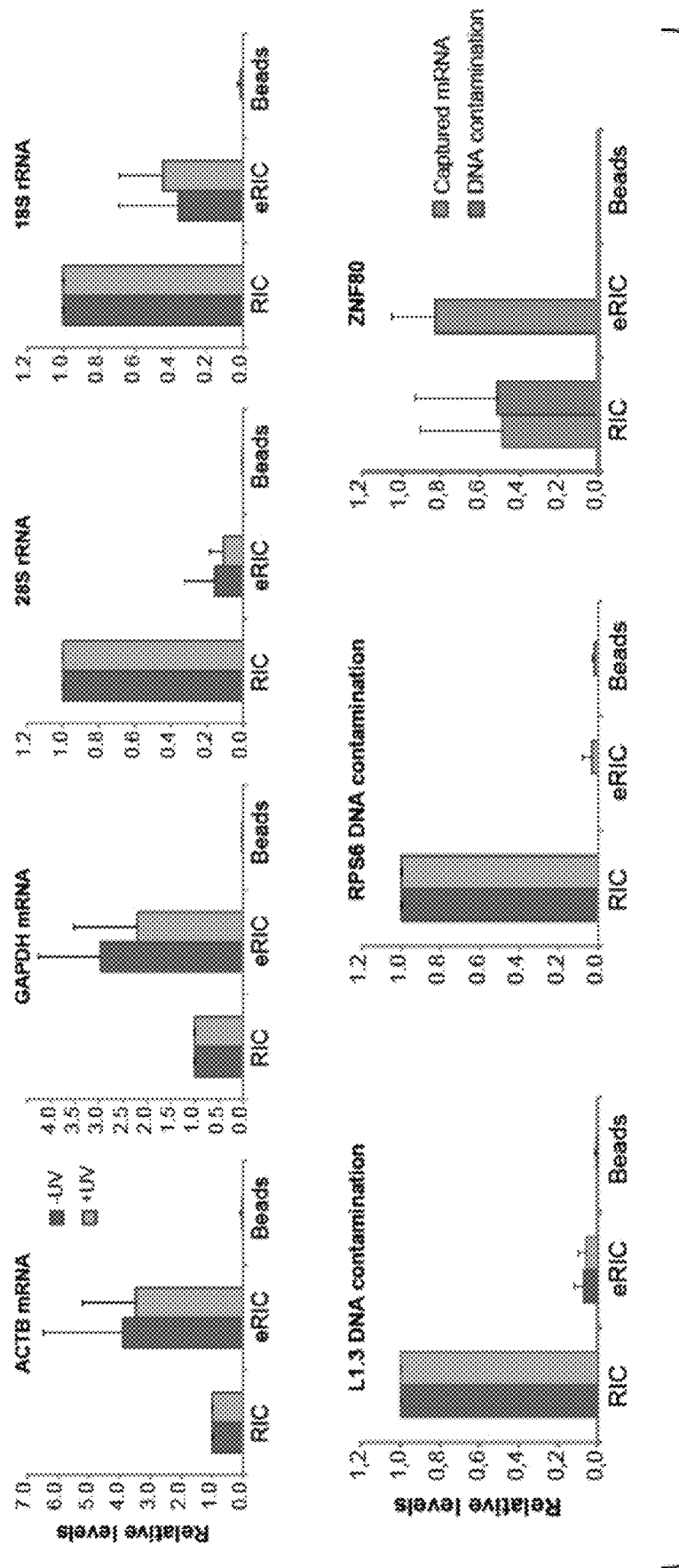

Profound reduction of rRNA and genomic DNA contamination by eRIC The inventors first compared the RNA capture characteristics of the two protocols. Although the eRIC elution per se is RNase-mediated, an aliquot of purified eRIC material was heat-eluted to allow RNA analyses. Aliquots of the RIC and eRIC heat eluates were assessed in a bioanalyzer, or reversely transcribed and subjected to qPCR using intron-sensitive primers that amplify cDNA but not genomic DNA. Pull down of poly(A) RNA by eRIC is specific and capture probe-mediated, because no RNA is detected when uncoupled beads are used (FIG. 9c). Compared to RIC, eRIC exhibits a profoundly different RNA elution profile (FIG. 9b,c). While about 30% of the total RNA eluted by RIC corresponds to rRNA, it is only around 3% in the eRIC samples. Indeed, the bioanalyzer pattern for eRIC is dominated by an evenly distributed smear between ~500-4,000 nucleotides that the inventors attribute to polyadenylated RNAs, whereas RIC eluates predominantly show the rRNA bands (FIG. 9b). Capture of rRNA is UV-independent and, interestingly, depletion of the 28S rRNA is more drastic than of the 18S rRNA (FIG. 9b,c). These data suggest that 18S rRNA co-purifies with poly(A) RNA either by means of a sufficiently long poly(A) stretch that is bound by the capture probe, or by hybridization of the rRNA to complementary sequences within poly(A) RNA. In line with these considerations, efforts to further reduce 18S rRNA contamination were met by decreased poly(A) RNA yields. The qPCR results show that the higher temperature used in the eRIC protocol is not associated with RNA degradation (FIG. 9c).

DNA contamination was then estimated by qPCR analysis for multiple genes on aliquots of RIC and eRIC eluates without prior reverse transcription. The results demonstrate that eRIC dramatically reduces the contamination with genomic DNA by 10-100 fold (FIG. 9c, lower panel). By contrast, DNA contamination in RIC can reach the level of the cDNA for genes with low expression levels, as indicated by the levels of genomic DNA and cDNA for ZNF80 (FIG. 9c).

Overall, these results highlight that eRIC leads to a profound reduction in rRNA and genomic DNA contamination without compromising and possibly enhancing the capture of poly(A) RNA. Since the RNA analyses required heat rather than RNase elution of the eRIC samples for obvious reasons, the purity of eRIC samples may be even higher following the RNase-based elution of the original eRIC protocol.

Analysis of RBPs Identified by RIC Versus eRIC

Figure 9D:
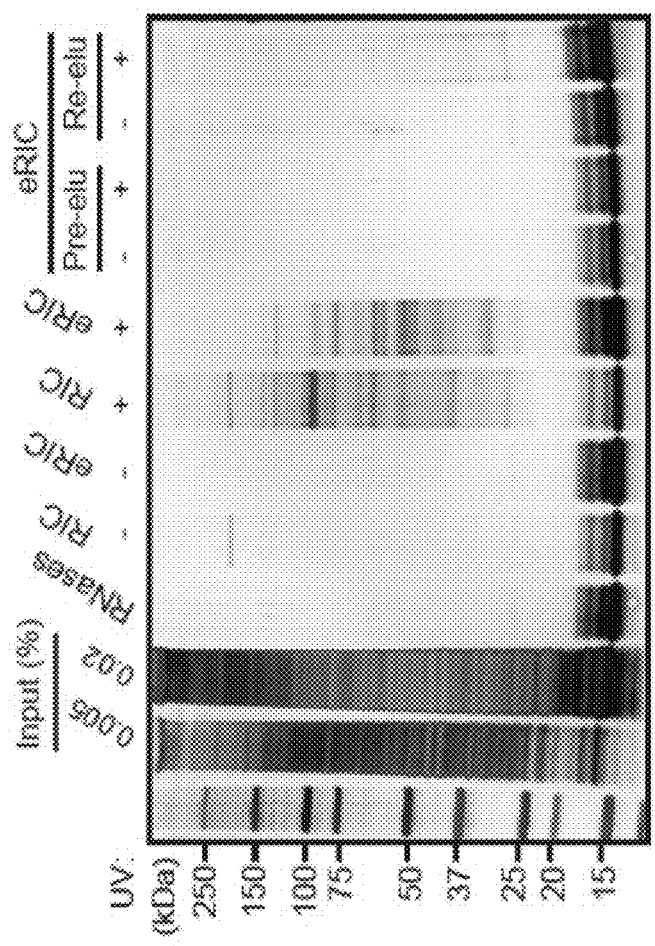

The inventors then subjected the proteins eluted according to the two protocols to downstream analysis. Following eRIC, the eluates are vacuum-concentrated using a Speed-Vac, instead of the Amicon filters that RIC employs and that are commonly associated with protein loss and size bias. To exclude technical bias, SpeedVac-mediated concentration was also applied to RIC samples (see below). SDS-PAGE and silver staining of eluted proteins shows patterns that differ profoundly from the input samples, and that are absent from the non-irradiated controls, indicating the enrichment of specific RBPs after UV crosslinking by both RIC and eRIC (FIG. 9d). Somewhat surprisingly, the band pattern of the eRIC and RIC eluates differs substantially (FIG. 9d), including proteins captured more efficiently by eRIC compared to RIC, and vice versa. The inventors also noticed that heat (re-)elution after the RNase-based elution of the eRIC samples yielded some proteins with similar migration as proteins eluted from the RIC samples (FIG. 9d), suggesting that these proteins are not RNA-bound. Therefore, RNase-mediated elution appears to be more specific for bona fide RBPs.

Figure 9E:
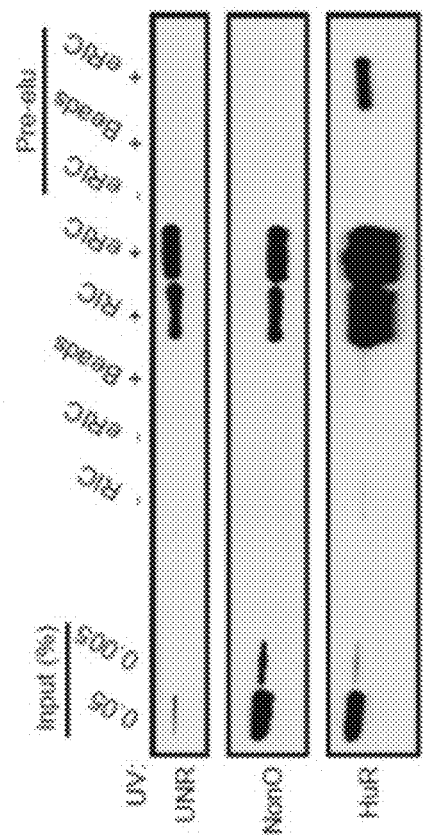

Specific enrichment for the known RBPs UnR, Nono and HuR was confirmed in both the RIC and the eRIC samples by western blotting. Pull down of the RBPs by eRIC was at least equally efficient than for RIC (FIG. 9e).

To minimize pre-analytical sample loss, the inventors introduced the highly sensitive Single-Pot Solid-Phase-enhanced Sample Preparation (SP3) protocol[11]. SP3 maximizes recovery of peptides for mass spectrometry and is compatible with the use of detergent throughout the procedure until the final wash. To facilitate the comparison between all other aspects of the RIC and eRIC protocols, and as described for the concentration step, SP3 was applied to both eRIC and RIC samples. Consequently, the inventors used equal cell numbers for both methods, focusing on the differences in RNP capture per se.

Figure 10B:
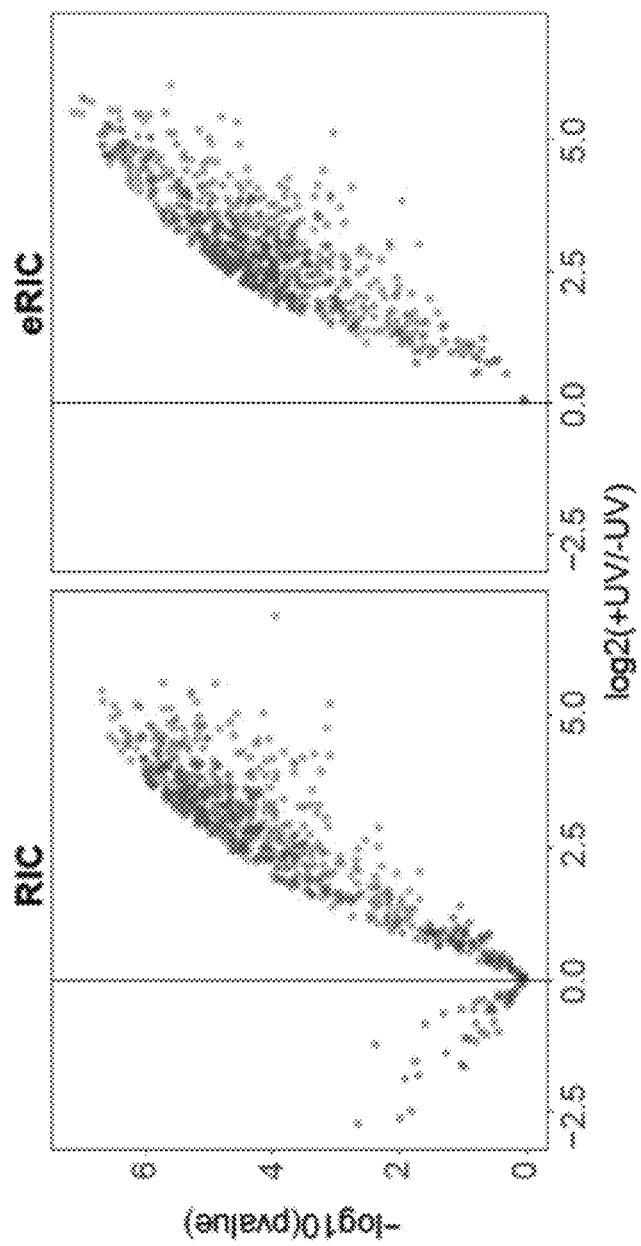
Figure 10A:
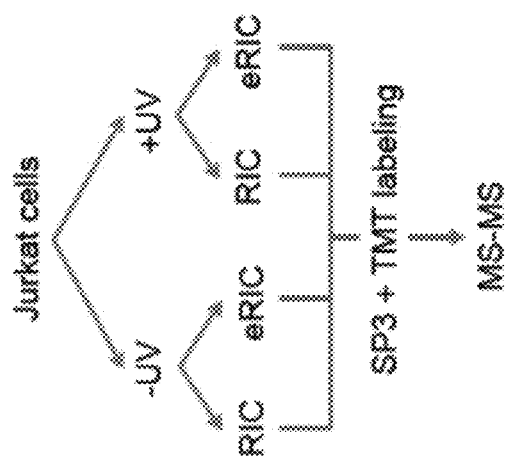
Figures 10C, 10D, 10E:
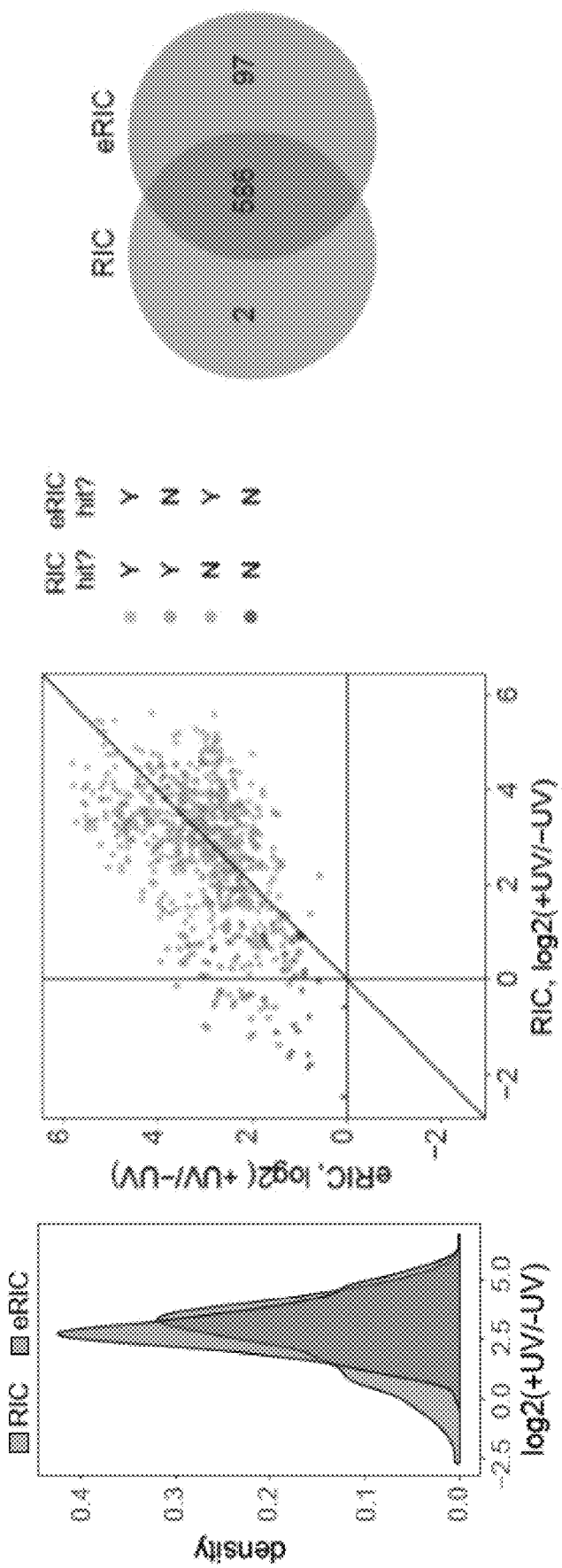
Figure 10G:
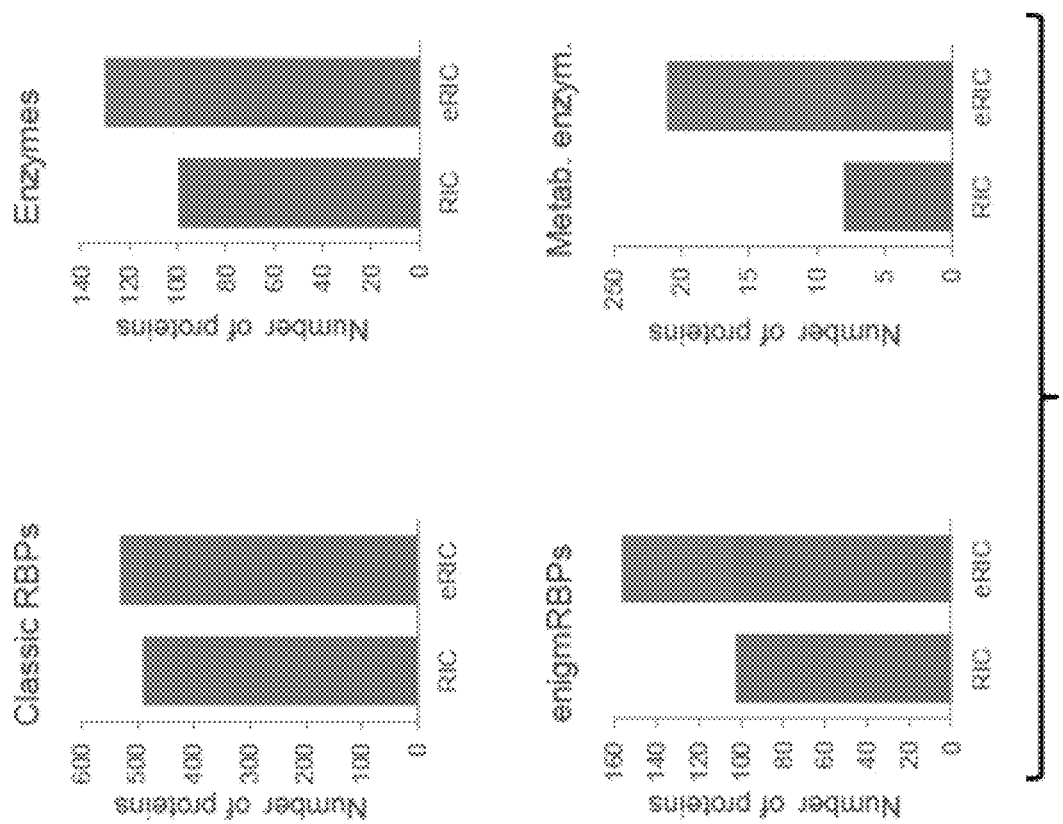
Figure 10F:
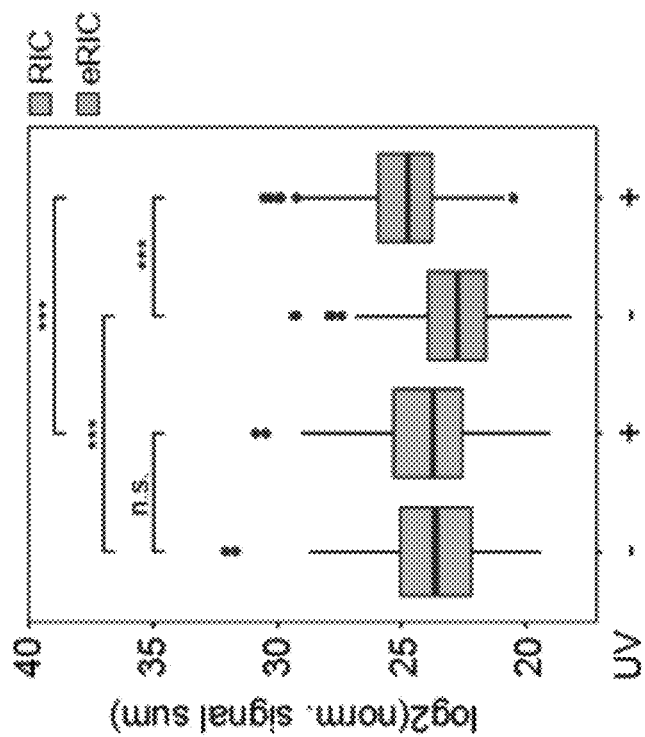

Protein eluates from two independent biological experiments each following the two different protocols were labeled by 10-plex tandem mass tag (TMT), and subjected to liquid chromatography-tandem mass spectrometry (LC-MS/MS) (FIG. 10a). Proteins that were significantly enriched in the crosslinked sample compared to the −UV control (false discovery rate (FDR) 0.05 and fold change (FC)>2) were considered as 'hits'. Applying this criterion, the inventors identified 683 and 588 RBPs in eRIC and RIC samples, respectively (FIG. 10b,d-e). The inventors had anticipated that the more stringent eRIC purification procedure might reduce the number of identified RBPs, but the contrary was observed. Detailed data analysis reveals that the unique eRIC hits were also detected in the RIC samples, but that higher background levels in the −UV controls precluded their enrichment in +UV RIC samples and excluded them as statistically significant hits (FIG. 10c). When the inventors compared the intensities of irradiated and non-irradiated samples of the 97 hits unique to eRIC, the normalized signal sum of these 97 proteins was significantly lower in the −UV control of eRIC in relation to RIC, while the opposite was observed in the irradiated samples (FIG. 10f). Thus, eRIC yields a dual benefit, reducing background and enhancing the specific pull down after crosslinking.

The inventors then investigated the ontology of the RIC and eRIC hits. While classical RBPs (as defined by Gerstberger et al.[12]) were similarly identified by the two approaches (FIG. 10g), eRIC recovers more unorthodox RBPs, including enzyme and especially metabolic enzyme RBPs[4,5] (FIG. 10g). This enrichment is particularly striking for enzymes of carbon metabolism, including the glycolytic pathway and the TCA cycle, and enzymes involved in lipid, estrogen and inosine 5'-phosphate metabolism. The RNA-binding activity of at least some of these enzymes has previously been validated 4,13.

Figure 10H:
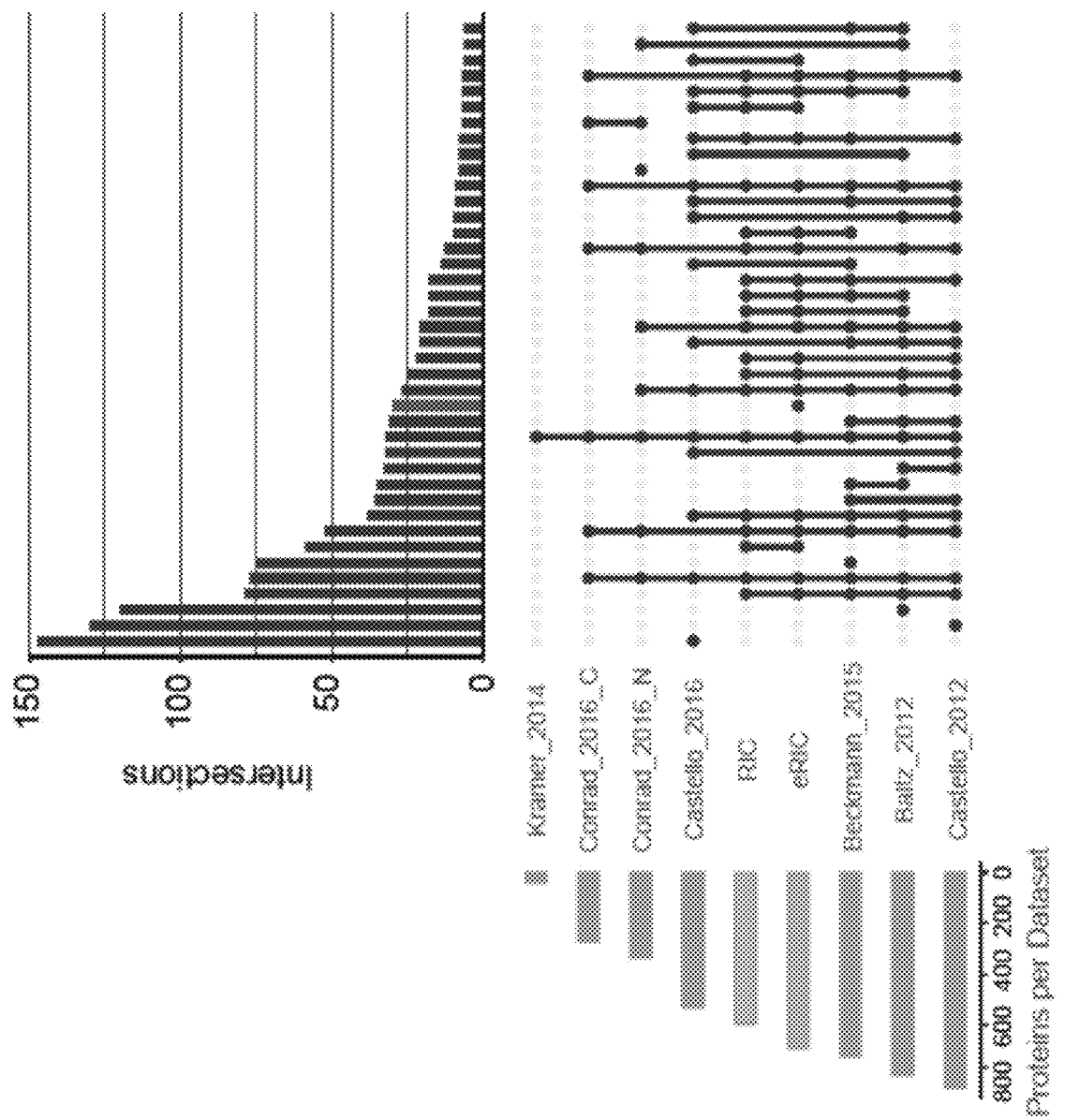
Figures 11A, 11B:
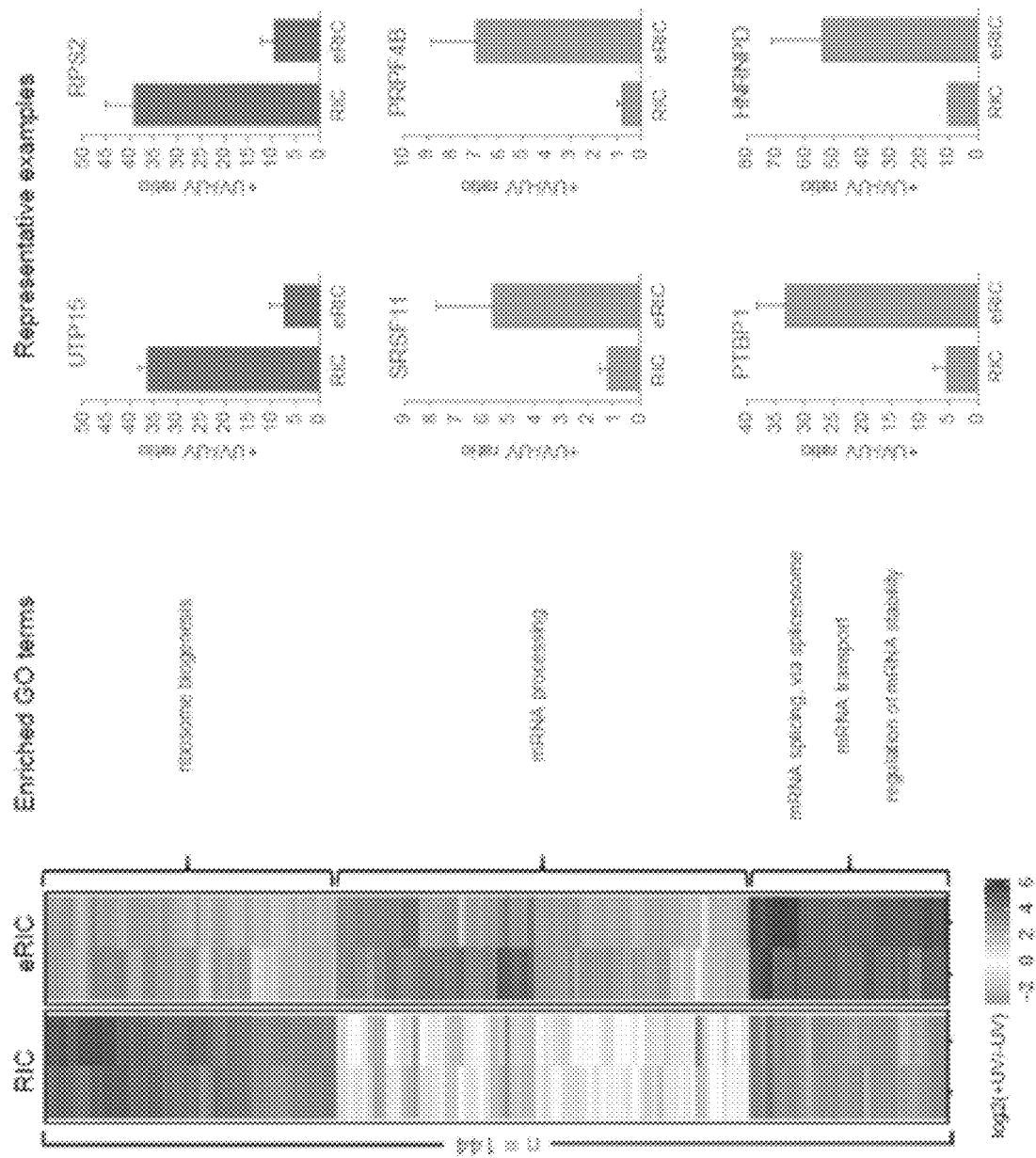

To evaluate whether eRIC detected new RBPs, the inventors compared the list of eRIC hits with those of previous RIC experiments conducted in human cells[1-4,14,15]. eRIC yielded 30 candidate RBPs that were not detected either in the previous experiments nor in the RIC dataset from the Jurkat cells analyzed here (FIG. 10h). Overall, the inventors identified 144 hits (FIG. 11) that differ significantly between eRIC and RIC (comparison of enrichment over −UV controls, FDR 0.05 and FC>2). Unsupervised clustering and posterior GO analysis of these proteins revealed a high enrichment for terms associated with mRNA, such as "mRNA-processing", "mRNA splicing" and "mRNA transport" amongst the proteins preferentially recovered by eRIC (FIG. 11a). In contrast, RIC enriches for proteins that are mostly associated with rRNA-related terms, such as "ribosome biogenesis" and "rRNA processing" (FIG. 11a). Representative examples of RBPs differentially captured by eRIC and RIC are shown in FIG. 11b. Thus, the pattern of RBPs recovered by eRIC and RIC reflects the nature of the RNAs captured with each method (FIG. 9).

eRIC Improves the Detection of Biological
Responses Within the RNA-Bound Proteome A major motivation for the development of eRIC was the need for an optimized method to detect dynamic biological responses of the RNA-binding proteome to different experimental conditions, and the inventors chose to evaluate the response of Jurkat cells to the α-ketoglutarate antagonist dimethyloxalylglycine (DMOG) as a test case, because α-ketoglutarate is required as a co-factor by RNA demethylases ([16,17]) and the inventors were curious to explore DMOG-induced changes in the RNA-bound proteomes. To reduce the influence of secondary effects, the inventors incubated proliferating Jurkat cells with a modest concentration (0.5 mM) of DMOG for only 6 hours. After crosslinking and lysis, the inventors compared eRIC and RIC using two complete sets of biological replicates (FIG. 12a). eRIC led to the identification of 716 and 710 RBPs in DMSO- and DMOG-treated cells, respectively, while 673 and 662 RBPs where identified under identical treatment conditions by RIC, confirming the enhanced detection of RBPs by eRIC.

Figure 12A:
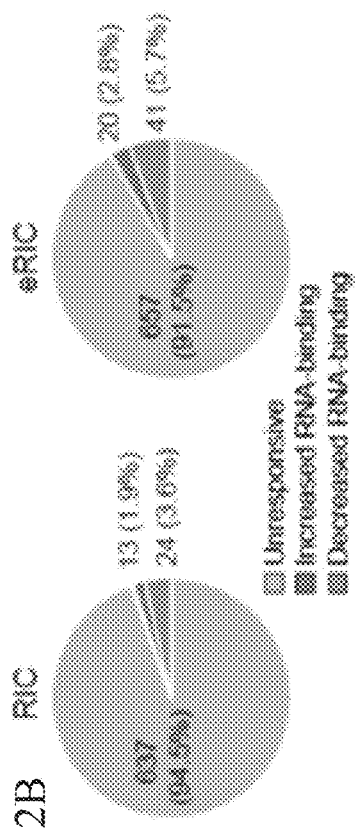
Figure 12B:
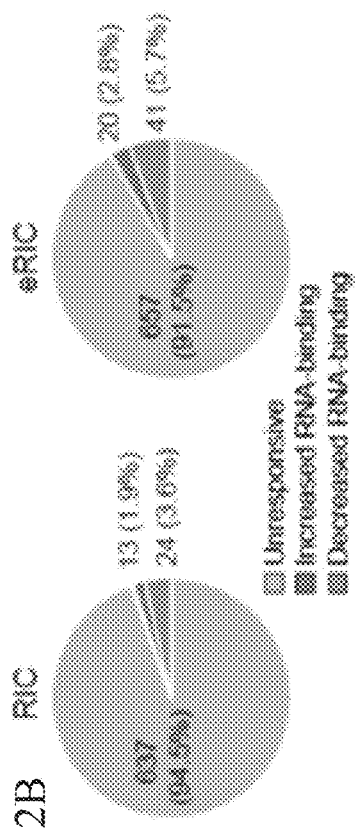
Figure 12C:
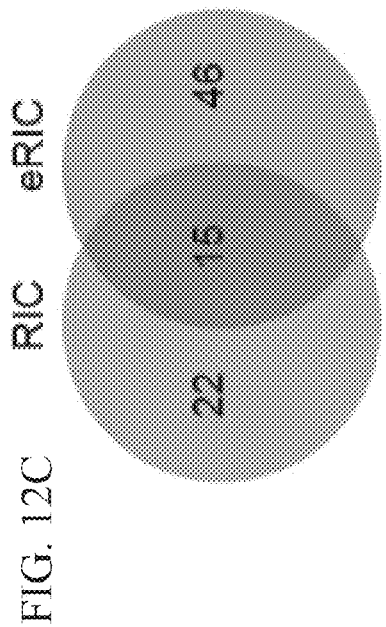
Figure 12D:
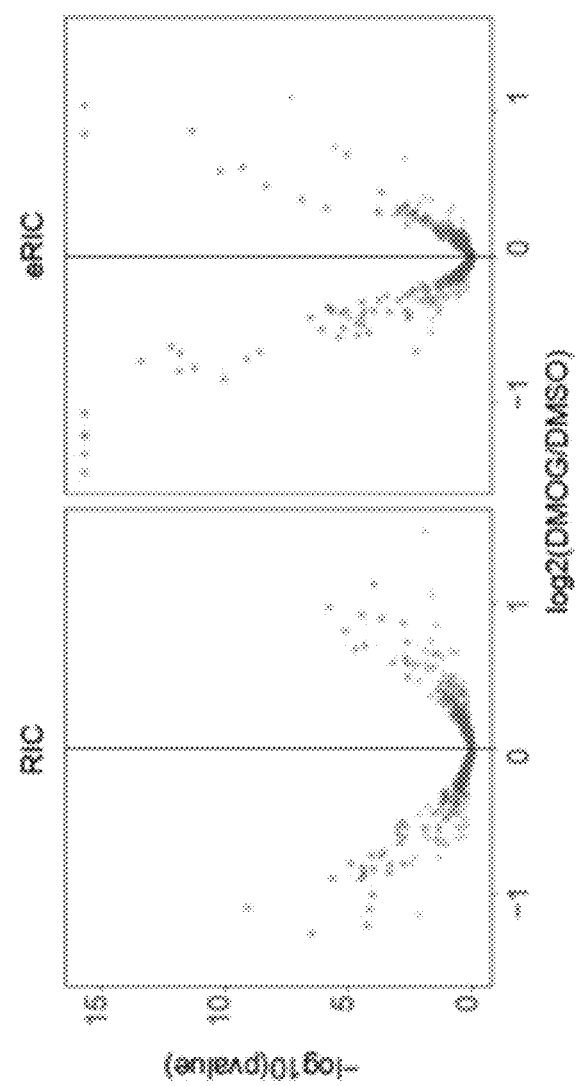
Figure 12E:
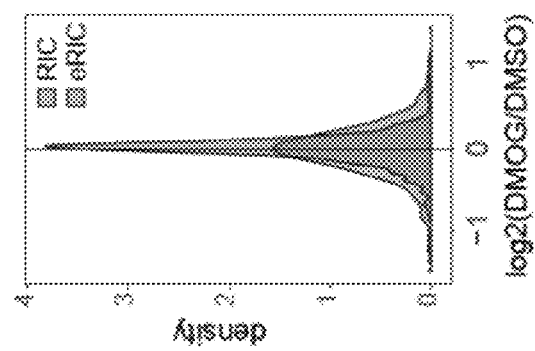
Figure 12F:
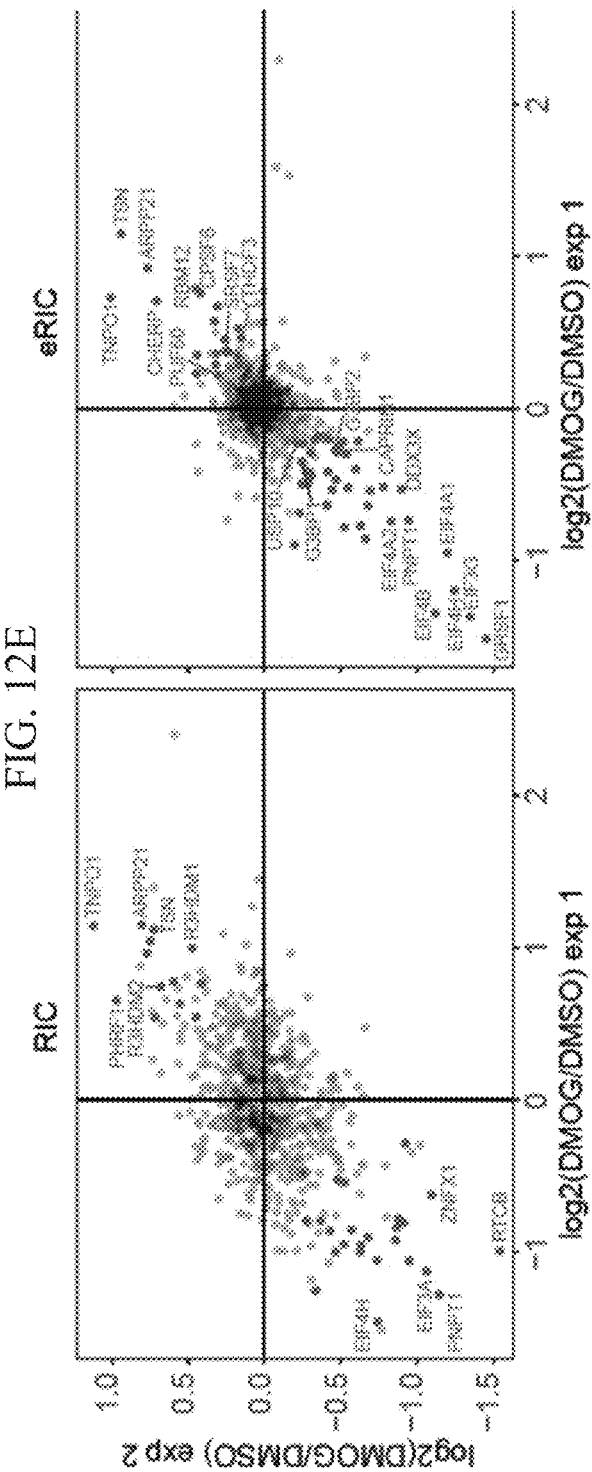

DMOG-responsive RBPs were defined in samples from UV-treated cells at a FDR of 0.05 and a consistent fold change of at least 10% in each replicate. eRIC recovered a specific group of 20 RBPs with increased and of 41 RBPs with decreased RNA-binding after DMOG treatment (FIG. 12b), compared to 13 and 24 responsive RBPs, respectively, identified by RIC (FIG. 12b). The hits obtained by the two protocols display striking differences and only modest overlap (FIG. 12c). To better understand these differences, the inventors compared the distribution of the differential ion intensities in eRIC and RIC eluates. These analyses showed reduced signal scatter and higher experimental reproducibility for the RBPs captured by eRIC (FIG. 12d-f), which increased the detection sensitivity for changes of the RNA-bound proteome.

Figure 12G:
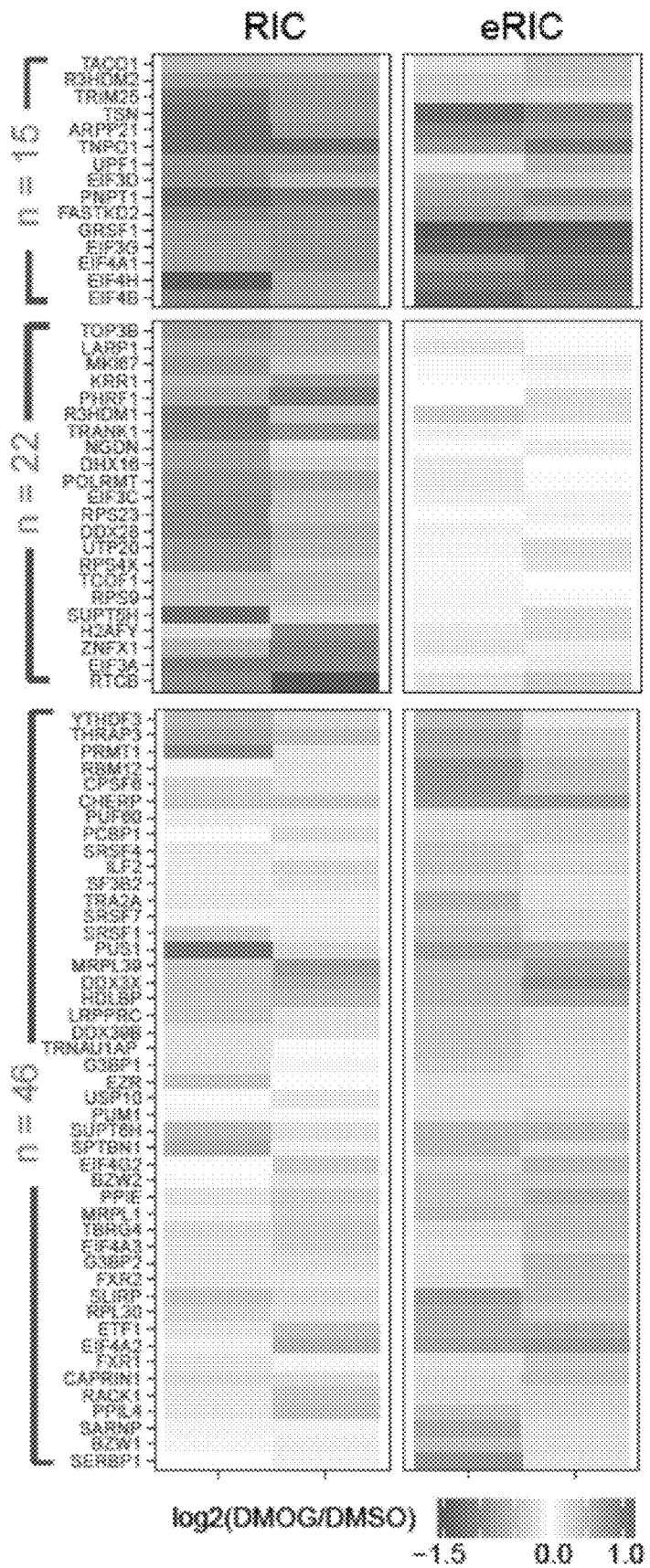
Figure 12H:
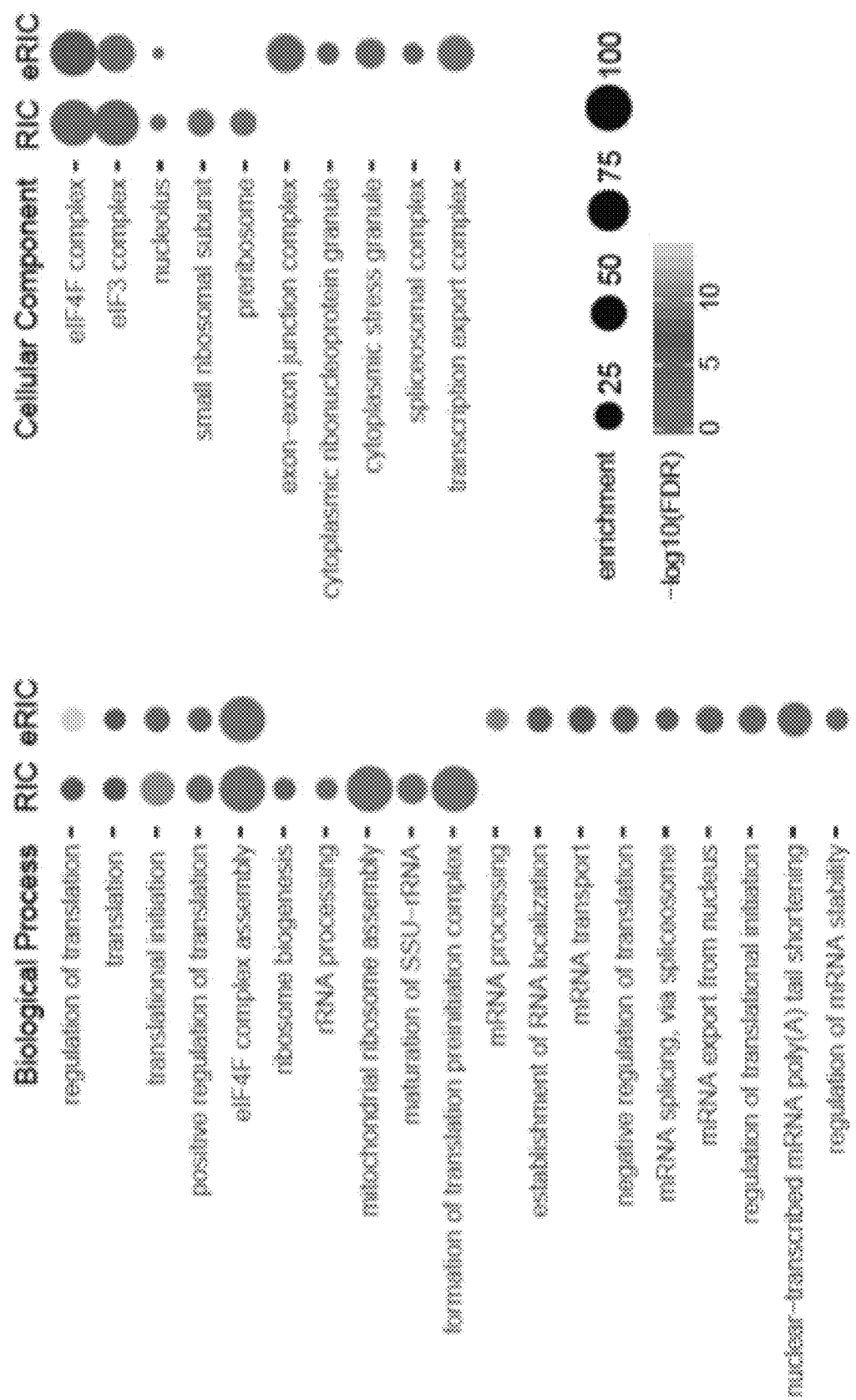

For the 22 differential hits that were only recovered by RIC (FIG. 12c), the inventors were struck by their complete lack of response in the eRIC samples (FIG. 12g). GO analysis revealed enrichment for rRNA-related terms and for constituents of the ribosome, pre-ribosome and nucleolus (FIG. 12h), suggesting that they do not directly bind to poly(A) RNA and potentially co-purify with the contaminating rRNA (FIG. 9). GO analysis of hits shared between RIC and eRIC showed association with mRNA translation, especially for eIF3 and eIF4 (FIG. 12h,i). By contrast, eRIC-specific hits were enriched for mRNA-related functions such as mRNA transport and mRNA splicing, or belong to complexes/structures that regulate mRNA metabolism, such as the spliceosomal complex and stress granules (FIG. 12h,i).

Figure 12I:
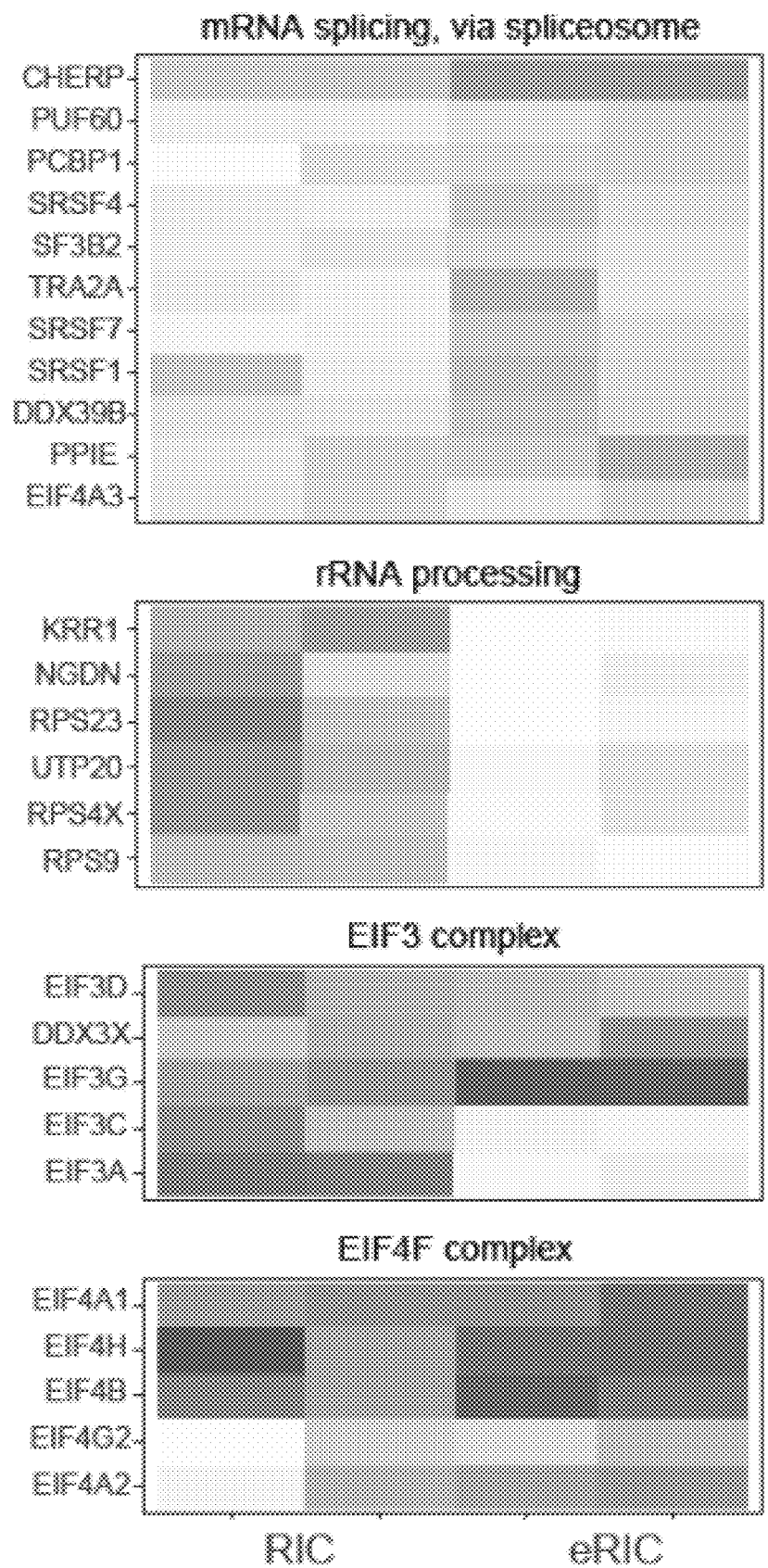

Taken together, eRIC facilitates sensitive comparative analyses of changes of the mRNA-bound proteome that escape RIC.

eRIC Reveals Diminished Binding of eIF3 and eIF4 to mRNA and Implicates Inhibition of the mTOR Pathway by DMOG DMOG treatment profoundly diminished the RNA binding of several translation initiation factors, especially of eIF3 and eIF4 (FIG. 12i). Since DMOG has been reported to negatively affect the activity of the mTOR kinase[18], which phosphorylates the inhibitory protein 4EBP, the inventors examined Western blots for 4EBP phosphorylation. Indeed, following treatment with 0.5 mM DMOG for 6 hours, phosphorylation of 4EBP is severely reduced. In addition, the inventors observe reduced phosphorylation of the mTOR targets S6K and ULK1, as well as of the serine 2448 of TOR itself (associated with TOR activation). These results indicate that DMOG inhibits mTOR and thus activates 4EBP, inhibiting translation initiation and explaining the reduced RNA binding of eIF3 and eIF4. These findings exemplify the value of the eRIC data to shed light on a biological process.

eRIC Identifies m6A-Responsive RBPs That Escape RIC

RNA demethylases are alpha-ketoglutarate-dependent dioxygenases that can be inhibited by DMOG[19]. Such inhibition would be expected to increase the steady state levels of N6-methyladenosine (m6A). The inventors tested this possibility using dot blot assays on poly(A) RNA purified from Jurkat cells treated with 0.5 mM DMOG (or DMSO) for 6 hours. This analysis indicated that DMOG incubation indeed increased the m6A modification of poly (A) RNA (FIG. 13a). The inventors were thus curious to see whether RBPs associated with m6A biology also responded to the DMOG treatment, especially since m6A was recently shown to affect the RNA-binding of different RBPs[20,21]. Strikingly, m6A-sensitive RBPs are significantly enriched amongst the eRIC hits (Fisher's exact test, p value=0.00016). Of the 61 DMOG-regulated RBPs that the inventors identified by eRIC, at least 18 (30%) were previously shown to be affected by m6A[20,21] (FIG. 13b). By contrast, only 2 of these were found by RIC (FIG. 13b). The direction of DMOG-induced changes corresponds well with predictions based on previous reports[20,21] (numbers in brackets in FIG. 13b). Representative examples of previously reported m6A readers (YTHDF3, CPSF6, PUF60, SRSF7) and m6A-repelled proteins (CAPRIN1, HDLBP, EIF4A1, G3BP2), as well as of proteins expected to be insensitive to m6A, are shown in FIG. 13c.

These results show that eRIC identifies changes of the poly(A) RNA-bound proteome concordant with the increase in steady state m6A levels which are missed by RIC, further supporting the superior performance of eRIC in comparative studies.

REFERENCES AS CITED 1. Baltz, A.G. et al. The mRNA-bound proteome and its global occupancy profile on protein-coding transcripts. *Mol Cell* 46, 674-90 (2012).

2. Castello, A. et al. Insights into RNA biology from an atlas of mammalian mRNA-binding proteins. *Cell* 149, 1393-406 (2012).
3. Conrad, T. et al. Serial interactome capture of the human cell nucleus. *Nat Commun* 7, 11212 (2016).
4. Beckmann, B. M. et al. The RNA-binding proteomes from yeast to man harbour conserved enigmRBPs. *Nat Commun* 6, 10127 (2015).
5. Hentze, M. W., Castello, A., Schwarzl, T. & Preiss, T. A brave new world of RNA-binding proteins. *Nat Rev Mol Cell Biol* 19, 327-341 (2018).
6. Reichel, M. et al. In Planta Determination of the mRNA-Binding Proteome of Arabidopsis Etiolated Seedlings. *Plant Cell* 28, 2435-2452 (2016).
7. Sysoev, V. O. et al. Global changes of the RNA-bound proteome during the maternal-to-zygotic transition in Drosophila. *Nat Commun* 7, 12128 (2016).
8. Liepelt, A. et al. Identification of RNA-binding Proteins in Macrophages by Interactome Capture. *Mol Cell Proteomics* 15, 2699-714 (2016).
9. Milek, M. et al. DDX54 regulates transcriptome dynamics during DNA damage response. *Genome Res* 27, 1344-1359 (2017).
10. Jacobsen, N. et al. Direct isolation of poly(A)+RNA from 4 M guanidine thiocyanate-lysed cell extracts using locked nucleic acid-oligo(T) capture. *Nucleic Acids Res* 32, e64 (2004).
11. Hughes, C. S. et al. Ultrasensitive proteome analysis using paramagnetic bead technology. *Mol Syst Biol* 10, 757 (2014).
12. Gerstberger, S., Hainer, M. & Tuschl, T. A census of human RNA-binding proteins. *Nat Rev Genet* 15, 829-45 (2014).
13. Chang, C. H. et al. Posttranscriptional control of T cell effector function by aerobic glycolysis. *Cell* 153, 1239-51 (2013).
14. Castello, A. et al. Comprehensive Identification of RNA-Binding Domains in Human Cells. *Mol Cell* 63, 696-710 (2016).
15. Kramer, K. et al. Photo-cross-linking and high-resolution mass spectrometry for assignment of RNA-binding sites in RNA-binding proteins. *Nat Methods* 11, 1064-70 (2014).
16. Gerken, T. et al. The obesity-associated FTO gene encodes a 2-oxoglutarate-dependent nucleic acid demethylase. *Science* 318, 1469-72 (2007).
17. Maity, A. & Das, B. N6-methyladenosine modification in mRNA: machinery, function and implications for health and diseases. *FEBS J* 283, 1607-30 (2016).

18. Duran, R. V. et al. HIF-independent role of prolyl hydroxylases in the cellular response to amino acids. *Oncogene* 32, 4549-56 (2013).

19. Elkashef, S. M. et al. IDH Mutation, Competitive Inhibition of FTO, and RNA Methylation. *Cancer Cell* 31, 619-620 (2017).

20. Arguello, A. E., DeLiberto, A. N. & Kleiner, R. E. RNA Chemical Proteomics Reveals the N(6)-Methyladenosine (m(6)A)-Regulated Protein-RNA Interactome. *J Am Chem Soc* 139, 17249-17252 (2017).

21. Edupuganti, R. R. et al. N(6)-methyladenosine (m(6) A) recruits and repels proteins to regulate mRNA homeostasis. *Nat Struct Mol Biol* 24, 870-878 (2017).

22. Singh, G., Pratt, G., Yeo, G. W. & Moore, M. J. The Clothes Make the mRNA: Past and Present Trends in mRNP Fashion. *Annu Rev Biochem* 84, 325-54 (2015).

23. Bao, X. et al. Capturing the interactome of newly transcribed RNA. *Nat Methods* 15, 213-220 (2018).

24. Huang, R., Han, M., Meng, L. & Chen, X. Transcriptome-wide discovery of coding and noncoding RNA-binding proteins. *Proc Natl Acad Sci U S A* 115, E3879-E3887 (2018).

25. He, C. et al. High-Resolution Mapping of RNA-Binding Regions in the Nuclear Proteome of Embryonic Stem Cells. *Mol Cell* 64, 416-430 (2016).

26. Burger, K. et al. 4-thiouridine inhibits rRNA synthesis and causes a nucleolar stress response. *RNA Biol* 10, 1623-30 (2013).

27. Boom, R. et al. Rapid and simple method for purification of nucleic acids. *J Clin Microbiol* 28, 495-503 (1990).

28. Jourdain, A. A. et al. A mitochondria-specific isoform of FASTK is present in mitochondrial RNA granules and regulates gene expression and function. Cell Rep 10, 1110-21 (2015).

29. Popow, J. et al. FASTKD2 is an RNA-binding protein required for mitochondrial RNA processing and translation. *RNA* 21, 1873-84 (2015).

30. Patil, D. P., Pickering, B. F. & Jaffrey, S. R. Reading m(6)A in the Transcriptome: m(6)A-Binding Proteins. *Trends Cell Biol* 28, 113-127 (2018).

31. Castello, A. et al. System-wide identification of RNA-binding proteins by interactome capture. *Nat Protoc* 8, 491-500 (2013).

32. Franken, H. et al. Thermal proteome profiling for unbiased identification of direct and indirect drug targets using multiplexed quantitative mass spectrometry. *Nat Protoc* 10, 1567-93 (2015).

33. Ritchie, M. E. et al. limma powers differential expression analyses for RNA-sequencing and microarray studies. *Nucleic Acids Res* 43, e47 (2015).

34. Huber, W., von Heydebreck, A., Sultmann, H., Poustka, A. & Vingron, M. Variance stabilization applied to microarray data calibration and to the quantification of differential expression. *Bioinformatics* 18 Suppl 1, S96-104 (2002).

35. Strimmer, K. fdrtool: a versatile R package for estimating local and tail area-based false discovery rates. *Bioinformatics* 24, 1461-2 (2008).

36. Ginestet, C. ggplot2: Elegant Graphics for Data Analysis. *Journal of the Royal Statistical Society Series a-Statistics in Society* 174, 245-245 (2011).

37. Conway, J. R., Lex, A. & Gehlenborg, N. UpSetR: an R package for the visualization of intersecting sets and their properties. *Bioinformatics* 33, 2938-2940 (2017).

38. Noh, J. H. et al. HuR and GRSF1 modulate the nuclear export and mitochondrial localization of the lncRNA RMRP. *Genes Dev* 30, 1224-39 (2016).

ADDITIONAL REFERENCES AS CITED

Jacobsen N., et al., Direct isolation of poly(A)+RNA from 4 M guanidine thiocyanate-lysed cell extracts using locked nucleic acid-oligo(T) capture. Nucleic Acids Res. 2004 Apr. 19;32(7):e64.

Jacobsen N., et al., Efficient poly(A)+RNA selection using LNA oligo(T) capture. Methods Mol Biol. 2011;703: 43-51.

Castello A, et al. Insights into RNA biology from an atlas of mammalian mRNA-binding proteins. Cell. 2012 Jun 8;149(6):1393-406. doi: 10.1016/j.cell.2012.04.031. Epub 2012 May 31.

Castello A, et al. System-wide identification of RNA-binding proteins by interactome capture. Nat Protoc. 2013 Mar;8(3):491-500.

The invention claimed is:

1. A method of detecting proteins that interact with poly(A) RNAs (RBPs) in a cell, tissue or organism, comprising:
   a) covalently cross-linking the contents of a cell, tissue or organism comprising RBPs using irradiation to produce biological material comprising cross-linked ribonucleotide complexes;
   b) lysing said biological material comprising said cross-linked ribonucleotide complexes;
   c) contacting said cross-linked ribonucleotide complexes under conditions at temperatures of above 15° C. with at least one oligo deoxythymidine (dT) probe, wherein said oligo (dT) probe comprises a locked nucleic acid (LNA)-thymine nucleotide analogue at every other position in the sequence thereof, wherein said oligo (dT) probe has a length of between 15 to 25 bases, and wherein said oligo (dT) probe is coupled to a solid support;
   d) performing a stringent pre-elution in pure water at about 40° C.;
   e) isolating complexes that comprise said at least one oligo (dT) probe using said solid support;
   f) enzymatically releasing and/or heat elution of said RBPs and RNA fragments from said isolated complexes to produce released RBPs; and
   g) detecting said released RBPs.

2. The method according to claim 1, wherein said irradiation is UV light.

3. The method according to claim 1, wherein said cells are lysed under denaturing conditions.

4. The method according to claim 1, further comprising a step of shearing genomic DNA before isolating said complexes.

5. The method according to claim 1, wherein said pre-elution is done for about 5 to 10 min.

6. The method according to claim 1, wherein said RBPs are released by RNA digestion.

7. The method according to claim 1, further comprising the step of centrifugation and/or vacuum concentrating the RBP samples.

8. The method according to claim 1, wherein analyzing said released RBPs comprises a preparation by Single-Pot Solid-Phase-enhanced Sample Preparation (SP3) and/or quantitative mass spectrometry.

9. The method according to claim 1, wherein said oligo (dT) probe has a length of 20 bases.

10. The method according to claim 1, wherein said heat elution is performed at the identical or lower temperature as the one that was used for the steps of the method before, and under less stringent salt conditions, whereby contaminant proteins are not co-eluted.

11. The method according to claim 1, further comprising the detection of changes in the RNA-association of the RBPs as detected, when compared with a control sample or a sample obtained under different experimental conditions.

* * * * *